(12) United States Patent
Mizumoto et al.

(10) Patent No.: US 8,790,577 B2
(45) Date of Patent: Jul. 29, 2014

(54) SAMPLE ANALYZER

(75) Inventors: Toru Mizumoto, Hyogo (JP); Ryuichiro Ebi, Osaka (JP); Keisuke Tsutsumida, Hyogo (JP); Yousuke Tanaka, Hyogo (JP); Junya Inoue, Hyogo (JP)

(73) Assignee: Sysmex Corporation, Kobe (JP)

( * ) Notice: Subject to any disclaimer, the term of this patent is extended or adjusted under 35 U.S.C. 154(b) by 700 days.

(21) Appl. No.: 12/283,478

(22) Filed: Sep. 12, 2008

(65) Prior Publication Data

US 2009/0074618 A1 Mar. 19, 2009

(30) Foreign Application Priority Data

Sep. 13, 2007 (JP) ................................. 2007-237344
Sep. 18, 2007 (JP) ................................. 2007-240638

(51) Int. Cl.
*G01N 15/06* (2006.01)
(52) U.S. Cl.
USPC ............... 422/68.1; 422/50; 422/63; 422/64; 422/65; 422/66; 436/43; 436/54; 436/47; 436/63; 436/66
(58) Field of Classification Search
USPC ............ 422/50, 63, 64, 65, 66, 67, 81, 82.01, 422/82.05, 68.1; 436/43, 54, 47, 63, 66, 67, 436/68, 69, 70, 71, 174, 180
See application file for complete search history.

(56) References Cited

U.S. PATENT DOCUMENTS

| | | | |
|---|---|---|---|
| 4,750,133 A * | 6/1988 | Eiskamp et al. | ............. 700/266 |
| 5,719,059 A | 2/1998 | Mimura et al. | |
| 5,891,733 A | 4/1999 | Inoue | |
| 6,442,440 B1 | 8/2002 | Miller | |
| 2004/0101440 A1 * | 5/2004 | Ishizawa et al. | ............... 422/64 |
| 2004/0191120 A1 | 9/2004 | Yanagawa | |
| 2004/0224351 A1 | 11/2004 | Shinohara | |
| 2005/0053521 A1 * | 3/2005 | Hirayama | ....................... 422/67 |
| 2005/0196821 A1 * | 9/2005 | Monfre et al. | ................. 435/14 |
| 2005/0219527 A1 | 10/2005 | Ikeuchi et al. | |

(Continued)

FOREIGN PATENT DOCUMENTS

CN 1340708 A 3/2002
EP 1190771 A1 3/2002

(Continued)

OTHER PUBLICATIONS

Office Action from counterpart Chinese Application No. 200810212323.1, dated Mar. 28, 2012, 12 pages.

Primary Examiner — Brian J Sines
(74) Attorney, Agent, or Firm — Brinks Gilson & Lione

(57) ABSTRACT

A sample analyzer is disclosed. In one embodiment, the sample analyzer includes an analysis section for analyzing a sample by using a reagent to obtain numerical data and distribution diagram of particles contained in the sample; a display device; an information receiver for receiving an input of reagent information assigned to the reagent; a determination section configured for determining whether or not the reagent satisfies a condition to determine that the reagent is a genuine product based on the reagent information; and a controller that controls the display device to display both the numerical data and the distribution diagram if the reagent satisfies the condition by the determination section and to display the numerical data without displaying the distribution diagram if the reagent does not satisfy the condition by the determination section.

17 Claims, 24 Drawing Sheets

(56) References Cited

U.S. PATENT DOCUMENTS

| | | |
|---|---|---|
| 2006/0004530 A1 | 1/2006 | Miyamoto et al. |
| 2006/0029520 A1* | 2/2006 | Tanoshima et al. ............. 422/63 |
| 2006/0064270 A1 | 3/2006 | Onomichi et al. |
| 2006/0210438 A1* | 9/2006 | Nagai et al. ..................... 422/73 |
| 2007/0078631 A1* | 4/2007 | Ariyoshi et al. ............... 702/189 |
| 2007/0110617 A1* | 5/2007 | Nagai et al. ..................... 422/65 |
| 2007/0255756 A1 | 11/2007 | Satomura et al. |
| 2008/0056944 A1* | 3/2008 | Nakamura et al. .............. 422/67 |
| 2008/0187951 A1* | 8/2008 | Nagai et al. ..................... 435/29 |
| 2008/0206098 A1* | 8/2008 | Tsutsumida et al. ........... 422/67 |
| 2008/0240984 A1 | 10/2008 | Wakamiya et al. |
| 2009/0035873 A1* | 2/2009 | Shibata ........................ 436/179 |
| 2009/0281930 A1* | 11/2009 | Sakagami ...................... 705/28 |

FOREIGN PATENT DOCUMENTS

| | | |
|---|---|---|
| JP | 63-138268 A | 6/1988 |
| JP | 09-026425 A | 1/1997 |
| JP | 2002-350451 A | 12/2002 |
| JP | 2004-012442 A | 1/2004 |
| JP | 2004-502179 A | 1/2004 |
| JP | 2004-294083 A | 10/2004 |
| JP | 2005-257450 A | 9/2005 |
| JP | 2006-017637 A | 1/2006 |
| JP | 2006-084253 A | 3/2006 |
| JP | 2006-084394 A | 3/2006 |
| JP | 2008-241670 A | 10/2008 |
| WO | WO 2006/009251 A1 | 1/2006 |

* cited by examiner

Genuine product determining operation flow

SAMPLE ANALYZER

RELATED APPLICATIONS

This application claims priority from Japanese Patent Application 2007-237344 filed on Sep. 13, 2007, and Japanese Patent Application 2007-240638 filed on Sep. 18, 2007. Each of the disclosure of these patent applications is herein incorporated by reference in its entirety.

TECHNICAL FIELD

The present invention relates to sample analyzers, in particular, to a sample analyzer for analyzing samples using reagent.

BACKGROUND

Sample analysis using reagent is widely known. In such sample analysis, the reagent to be used differs depending on the difference in analysis principle, analyzing method, configuration of the analyzer, and the like even when analyzing the same analyzing item. For instance, U.S. Pat. No. 5,891,733 discloses using a dedicated urine particle analyzing reagent in a predetermined analyzing method of the urine particle analysis.

A sample analyzer for analyzing the sample using a dedicated reagent is conventionally known (see e.g., US Patent Application Publication No. 2006/210438).

US Patent Application Publication No. 2006/210438 discloses a blood analyzer (sample analyzer) for analyzing blood using a dedicated reagent. In the blood analyzer, a plurality of measurement modes with different measurement items can be selected and the dedicated reagent used in each measurement mode is made common, so that reagent management is facilitated.

Conventionally, generally, in the sample analyzer for performing screening of samples, whether or not the obtained analysis result is to be output for use in diagnosis is determined by the laboratory technician, and is validated. In recent years, a sample analyzer is also known that has an automatic validation function capable of automatically validating the analysis result to alleviate the load of the laboratory technician.

The dedicated reagent is optimized for the sample analyzer in respect of the components and the like so that highly accurate analysis result can be obtained in the sample analyzer. Furthermore, in the sample analyzer using the dedicated reagent, the evaluation test is repeatedly carried out and the design of the sample analyzer is performed to guarantee that highly accurate analysis result can be obtained when analysis is performed using the dedicated reagent (genuine reagent or genuine product). Therefore, when the sample is analyzed with the sample analyzer using the reagent (non-dedicated reagent) other than the dedicated reagent which performance is guaranteed by the supplier of the sample analyzer, there is no guarantee that an accurate analysis result will be obtained, and the reliability of the analysis result lowers. However, in the conventional sample analyzer, even if a non-dedicated reagent of low measurement accuracy is used, the sample is analyzed similar to when the dedicated reagent of high measurement accuracy is used, and the analysis result is displayed. Furthermore, in the sample analyzer having an automatic validation function, the analysis result is validated even if a non-dedicated reagent of low measurement accuracy is used similar to when the dedicated reagent of high measurement accuracy is used by enabling the automatic validation function. In other words, the analysis result of low reliability tends to be automatically validated.

BRIEF SUMMARY

The scope of the present invention is defined solely by the appended claims, and is not affected to any degree by the statements within this summary.

A first sample analyzer embodying features of the present invention includes: an analysis section for analyzing a sample by using a reagent; an information receiver for receiving an input of information regarding the reagent; a determination section for determining, whether or not the reagent satisfies a condition to determine that the reagent is a genuine product, based on the information received by the information receiver; and a controller for controlling an operation of the sample analyzer based on a result of the determination by the determination section.

A second sample analyzer embodying features of the present invention includes: an analysis section for analyzing a sample by using a reagent; a display device for displaying an analysis result by the analysis section; an information receiver for receiving an input of information regarding the reagent; a determination section for determining, whether or not the reagent satisfies a condition to determine that the reagent is a genuine product, based on the information received by the information receiver; and a display controller for controlling the display device based on a result of the determination by the determination section; wherein the display controller controls the display so as to non-display at least one part of the display of the analysis result in the display device if determined that the reagent does not satisfy the condition by the determination section.

A third sample analyzer embodying features of the present invention includes: an analysis section for analyzing a sample by using a reagent; an information receiver for receiving an input of information regarding the reagent; a determination section for determining, whether or not the reagent satisfies a condition to determine that the reagent is a genuine product, based on the information received by the information receiver; and an automatic validation section for automatically validating the analysis result if determined that the reagent satisfies the condition by the determination section, and not automatically validating the analysis result if determined that the reagent does not satisfy the condition by the determination section.

BRIEF DESCRIPTION OF THE DRAWINGS

FIG. 19 is a view showing an analysis result screen of the urine particle analyzer according to one embodiment shown in FIG. 1;

DETAILED DESCRIPTION OF THE PREFERRED EMBODIMENTS

First Embodiment

The first embodiment of the present invention will be described based on the drawings.

Figure 1:
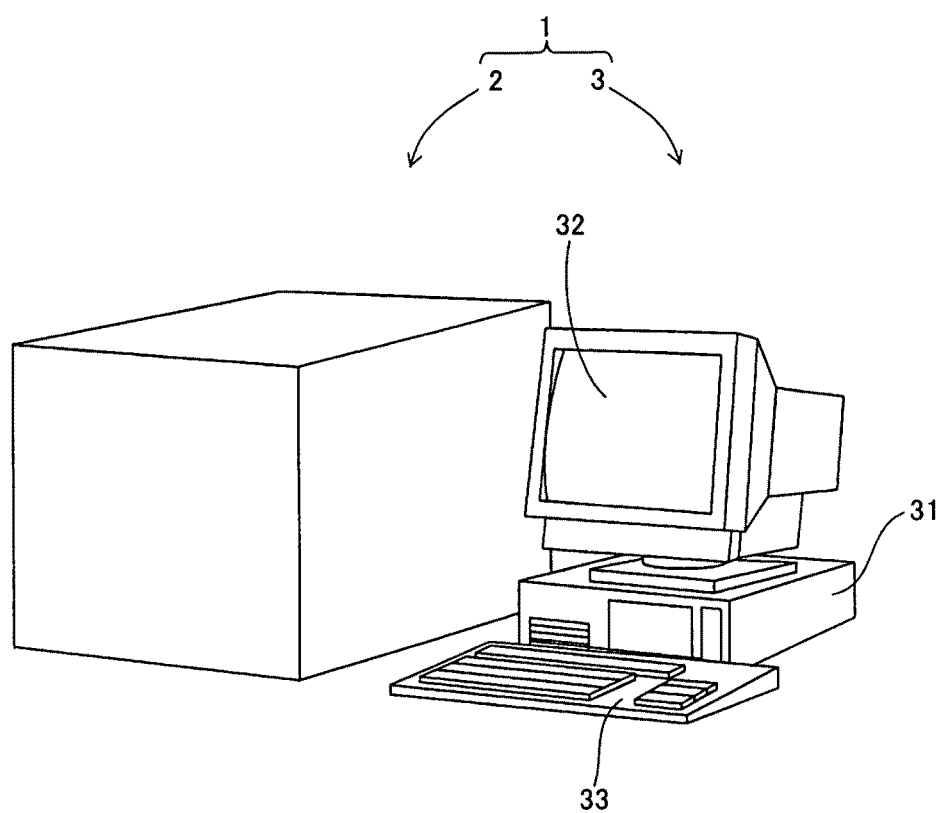
FIG. 1 is a perspective view showing a urine particle analyzer according to one embodiment of the present invention.

FIG. 1 is a perspective view showing a urine particle analyzer according to one embodiment of the present invention. FIGS. 2 to 9 are views describing the configuration of the urine particle analyzer according to one embodiment shown in FIG. 1. The configuration of the urine particle analyzer 1 according to one embodiment of the present invention will be described with reference to FIGS. 1 to 9.

As shown in FIG. 1, the urine particle analyzer 1 according to one embodiment of the present invention is configured by a measurement section 2 for optically measuring the particles contained in the urine by flow cytometry, and a data processing section 3 for processing a measurement value output from the measurement section 2 and obtaining the analysis result.

Figure 2:
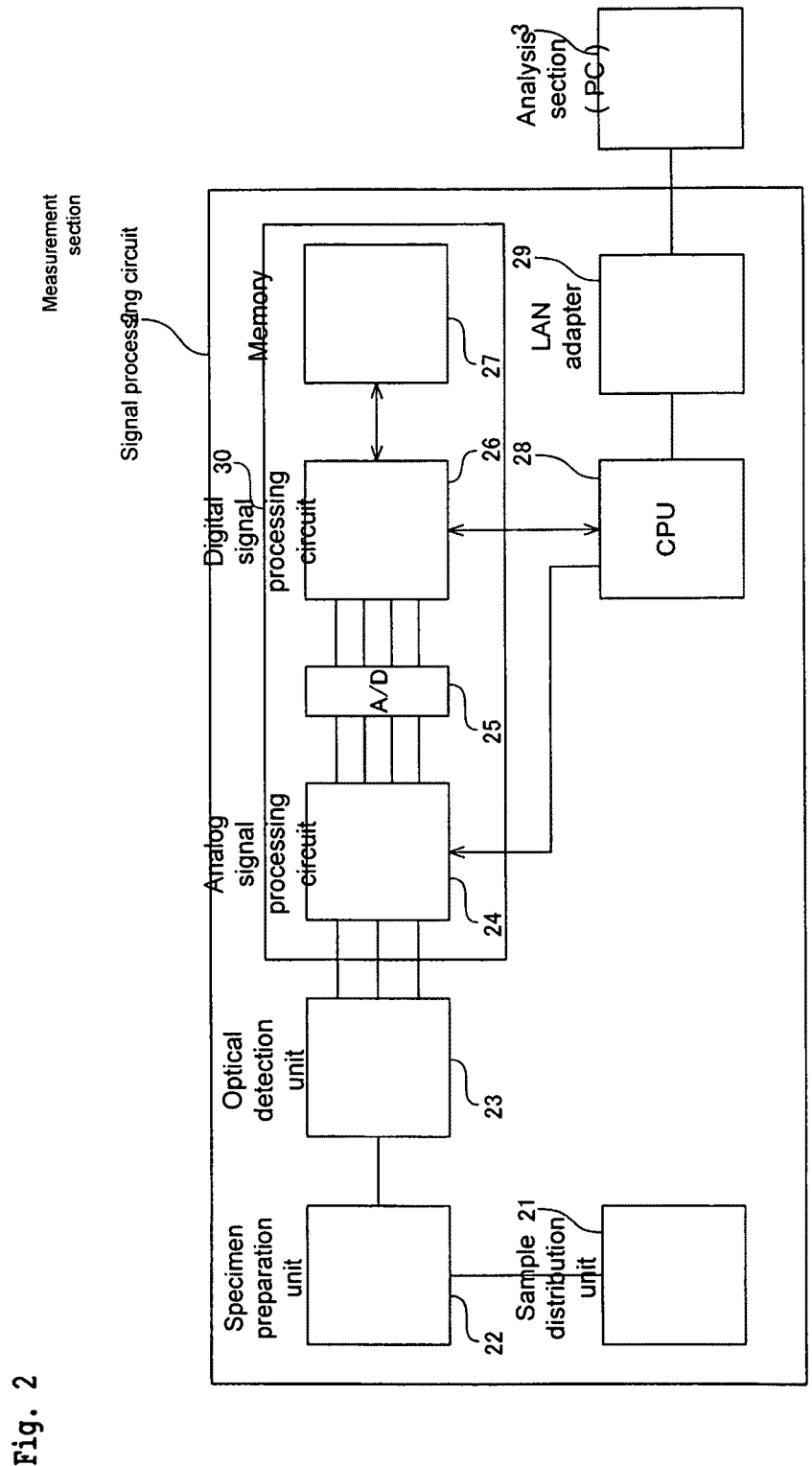
FIG. 2 is a block diagram showing a configuration of a measurement section of the urine particle analyzer according to one embodiment shown in FIG. 1.

As shown in FIG. 2, the measurement section 2 is arranged with a sample distribution unit 21, a specimen preparation unit 22, an optical detection unit 23, an analog signal processing circuit 24 for performing amplification, filtering, and the like on the output by the optical detection unit 23, an A/D converter 25 for converting the output of the analog signal processing circuit 24 to a digital signal, and a digital signal processing circuit 26 for performing a predetermined waveform process on the digital signal. The measurement section 2 is also arranged with a memory 27 connected to the digital signal processing circuit 26, a CPU 28 connected to the analog signal processing circuit 24 and the digital signal processing circuit 26, and a LAN adapter 29 connected to the CPU 28. The data processing section 3 is LAN connected to the measurement section 2 through the LAN adapter 29. The analog signal processing circuit 24, the A/D converter 25, the digital signal processing circuit 26, and the memory 27 configure a signal processing circuit 30 on an electric signal output by the optical detection unit 23.

The sample distribution unit 21 is configured to dispense the urine (sample) to the specimen preparation unit 22 by a predetermined distribution amount. The specimen preparation unit 22 prepares the measurement specimen from the urine (sample) dispensed by the sample distribution unit 21 and reagent, and supplies the prepared measurement specimen to a sheath flow cell 23c of the optical detection unit 23 to be hereinafter described along with sheath liquid.

Figure 3:
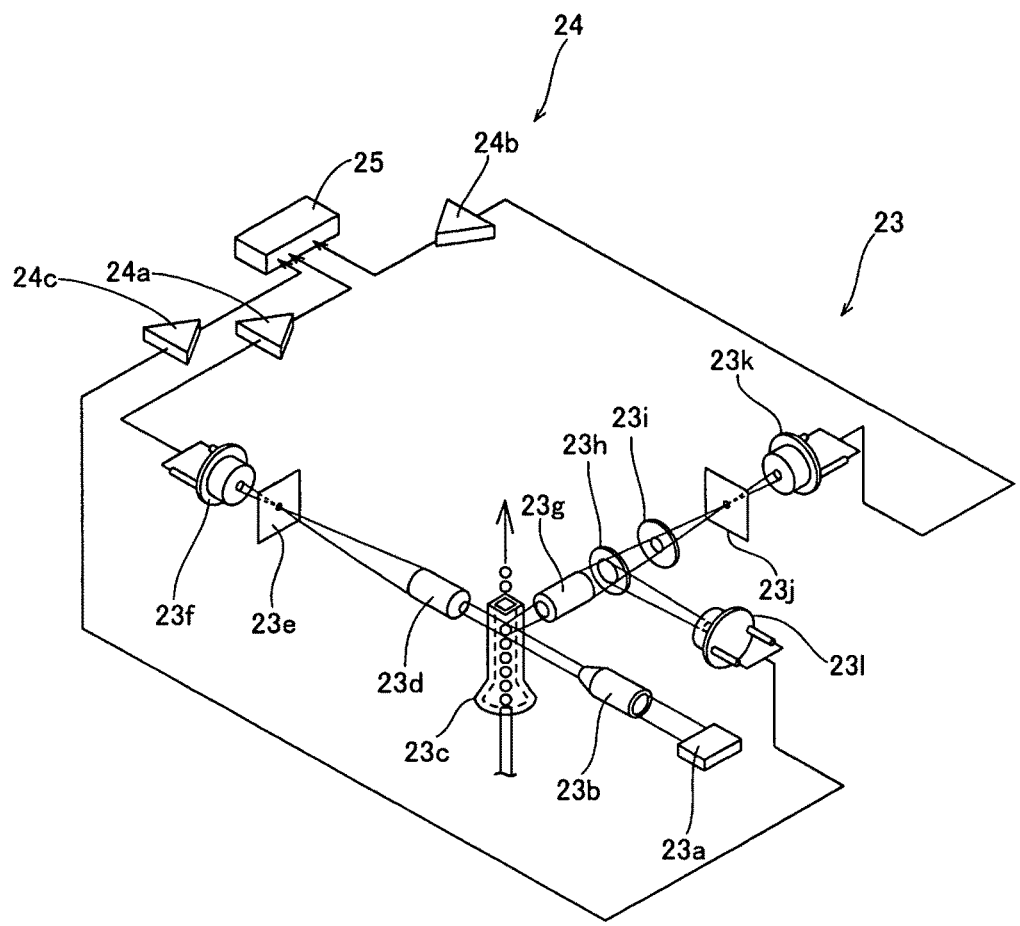
FIG. 3 is a view describing a configuration of the measurement section of the urine particle analyzer according to one embodiment shown in FIG. 1.

As shown in FIG. 3, the optical detection unit 23 includes a light emitting part 23a for emitting laser light, an irradiation lens unit 23b, the sheath flow cell 23c irradiated with laser light, a light collecting lens 23d arranged on an extended line in a traveling direction of the laser light emitted from the light emitting part 23a, a pin hole 23e and a PD (photodiode) 23f, a light collecting lens 23g arranged in a direction intersecting the traveling direction of the laser light emitted from the light emitting part 23a, a dichroic mirror 23h, an optical filter 23i, a pin hole 23j and a PD 23k, and an APD (avalanche photodiode) 23l arranged at the side of the dichroic mirror 23h.

The light emitting part 23a is arranged to emit light with respect to the specimen flow containing the measurement specimen passing through the sheath flow cell 23c. The irradiation lens unit 23b is arranged to parallelize the light emitted from the light emitting part 23a. The PDF 23f is arranged to receive a forward scattered light exit from the sheath flow cell 23c.

The dichroic mirror 23h is arranged to separate the lateral scattered light and the lateral fluorescent light emitted from the sheath flow cell 23c. Specifically, the dichroic mirror 23h is arranged to enter the lateral scattered light emitted from the sheath flow cell 23c to the PD 23k, and enter the lateral fluorescent light emitted from the sheath flow cell 23c to the APD 23l. The PD 23k is arranged to receive the lateral scattered light. The APD 23l is arranged to receive the lateral fluorescent light. The PD 23f, 23k, and the APD 23l respectively have a function of converting the received optical signal to an electric signal.

As shown in FIG. 3, the analog signal processing circuit 24 includes amplifiers 24a, 24b, and 24c. The amplifiers 24a, 24b, and 24c are respectively arranged to amplify and waveform process the electric signals output from the PD 23f, 23k, and the APD 23l.

The memory 27 is configured to store information (determination result information) indicating whether or not the changed new reagent is a dedicated reagent (genuine product). Specifically, the CPU 31a of the data processing section 3 to be hereinafter described determines whether or not the changed new reagent is a dedicated reagent. The memory 27 is configured to store the determination result information based on the result of determination by the CPU 31a.

Figure 4:
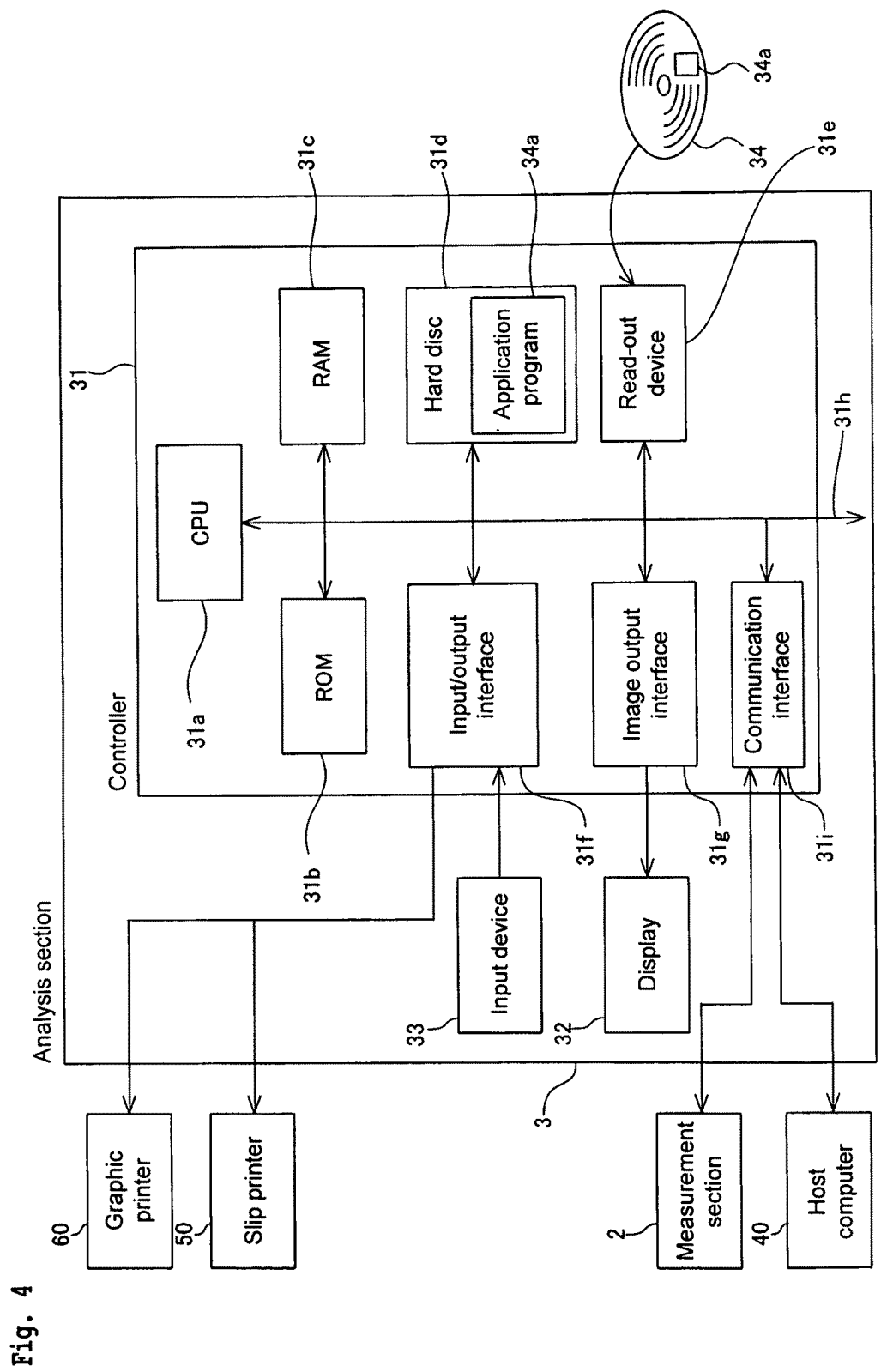
FIG. 4 is a block diagram showing a configuration of a data processing section of the urine particle analyzer according to one embodiment shown in FIG. 1.

As shown in FIG. 1, the data processing section 3 is configured by personal computer (PC), and the like. The data processing section 3 is configured by a controller 31, a display 32, and an input device 33. The data processing section 3 has functions of receiving operation of the user, transmitting operation command to the measurement section 2, receiving measurement data (measurement value) from the measurement section 2, processing the measurement data, and displaying the analysis result. As shown in FIG. 4, the controller 31 is configured by CPU 31a, ROM 31b, RAM 31c, hard disc 31d, read-out device 31e, input/output interface 31f, image output interface 31g, and a communication interface 31i. The CPU 31a, ROM 31b, the RAM 31c, hard disc 31d, read-out device 31e, input/output interface 31f, image output interface 31g, and communication interface 31i are data communicably connected by a bus 31h.

The CPU 31a is arranged to execute the computer programs stored in the ROM 31b and the computer program loaded in the RAM 31c. The ROM 31b is configured by mask ROM, PROM, EPROM, EEPROM, and the like, and is recorded with the computer program to be executed by the CPU 31a, data used for the same, and the like.

The CPU 31a has a function of processing the measurement value measured by the measurement section 2 and obtaining the analysis result. The CPU 31a has a function of outputting, to an image output interface 31g, a image signal corresponding to a analysis result screen SC1 for displaying the analysis result (see FIG. 5), a setting screen SC2 (see FIG. 6), and SC3 (see FIG. 7). The analysis result screen SC1 includes a display region SC1a for displaying the numerical data for basic items, a display region SC1b for displaying the numerical data for the research item, and a display region SC1c for displaying a scattergram showing distribution of number, size, and the like of the particles in the measurement specimen in the basic item. The basic item is a measurement item of high importance used in diagnosis. The research item is used as reference of diagnosis, and is an auxiliary measurement item of low importance compared to the basic item. In the analysis result screen SC1, the analysis results of RBC (red blood cells), WBC (white blood cells), EC (epidermal cells), CAST (casts), and BACT (bacteria) are shown as basic items. Furthermore, for research items, analysis results of X'TAL (crystal), YLC (yeast-like fungus), SRC (small round cells), Path. CAST (diseased cast including cell component), MUCUS (thread of mucus), SPERM (sperm), and Cond. (urine conductivity) are shown.

Figure 5:
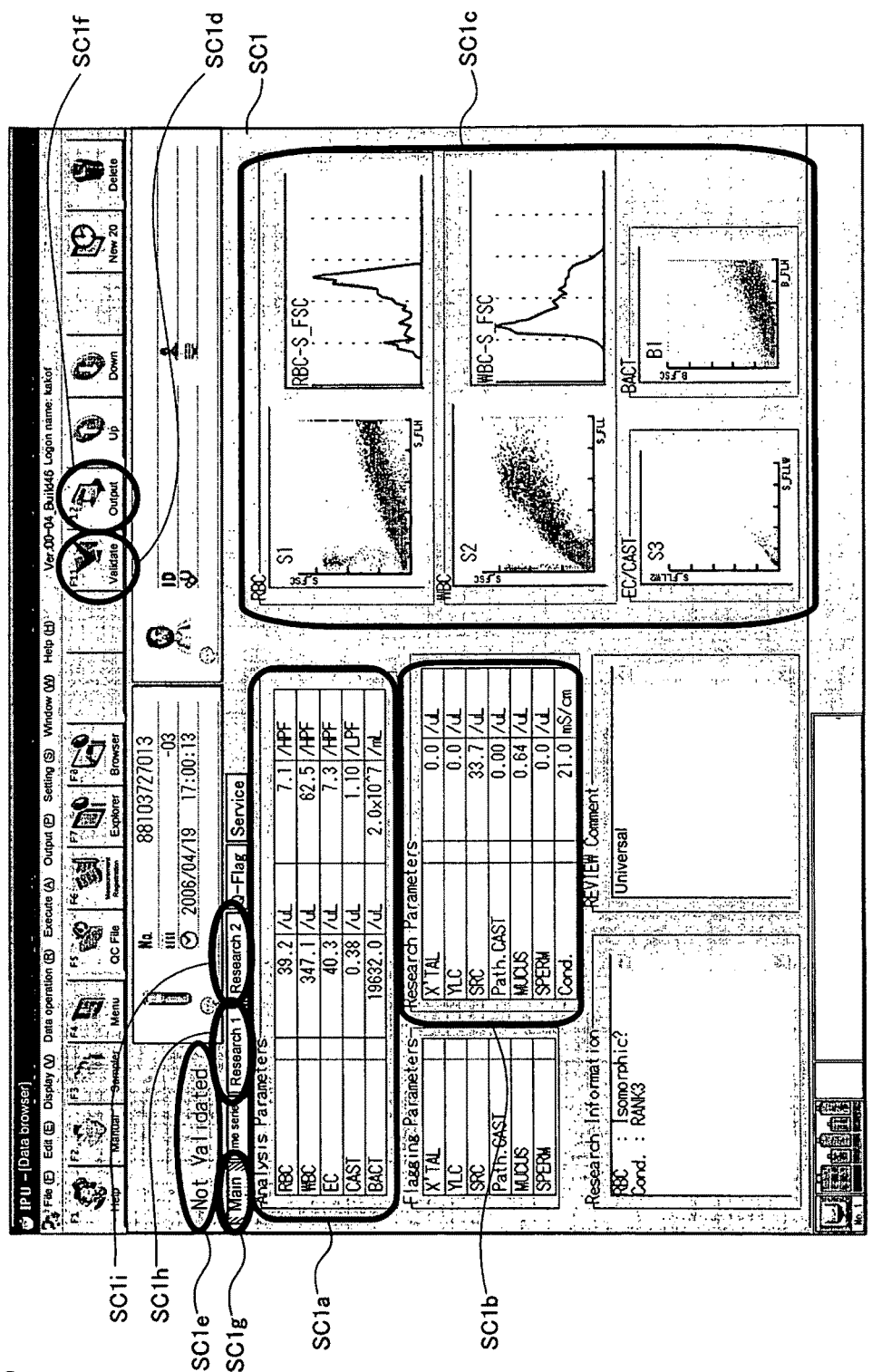
FIG. 5 is a view showing an analysis result screen of the urine particle analyzer according to one embodiment shown in FIG. 1.

In the urine particle analyzer 1 according to the present embodiment, a Validated display is displayed on the display region SC1e by pushing the validate button SC1d of the analysis result screen SC1. The validate button SC1d is a button that is pushed when the laboratory technician determines whether or not to output the analysis result to use for diagnosis, and determined to be output. As shown in FIG. 5, if the Validate button SC1d is not pushed, Not Validated display is displayed on the display region SC1e.

The urine particle analyzer 1 according to the present embodiment outputs the analysis result by pushing the output button SC1f when the Validated display is displayed on the display region SC1e shown in FIG. 5. The user can arbitrarily select whether to output the analysis result to the host computer 40 (see FIG. 4), to output to a slip printer 50 (see FIG. 4), or to output to a graphic printer 60 (see FIG. 4). If the Not Validated display is displayed on the display region SC1e, as shown in FIG. 5, the user cannot push the output button SC1f.

Figure 6:
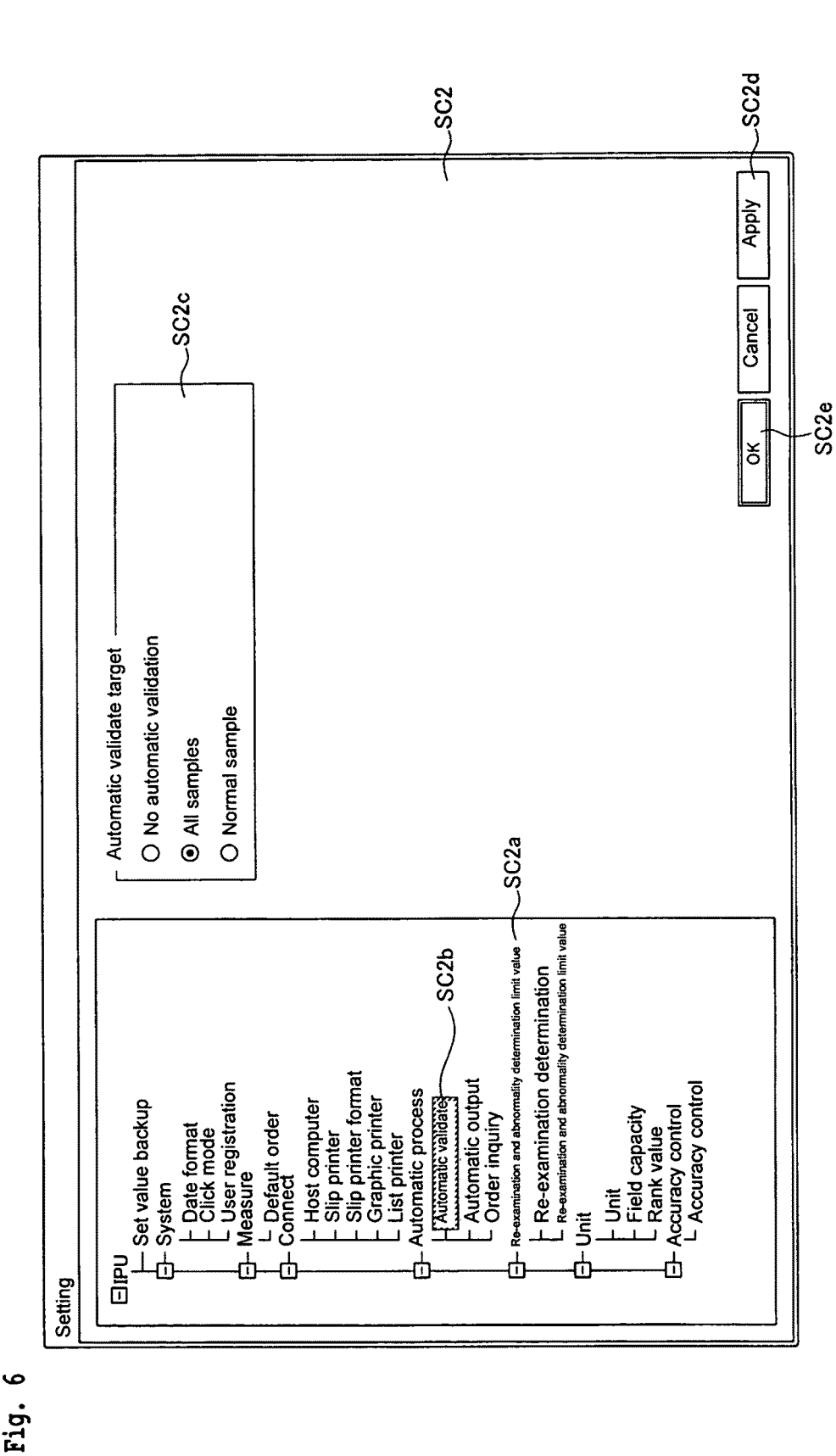
FIG. 6 is a view showing a setting screen of the urine particle analyzer according to one embodiment shown in FIG. 1.
Figure 7:
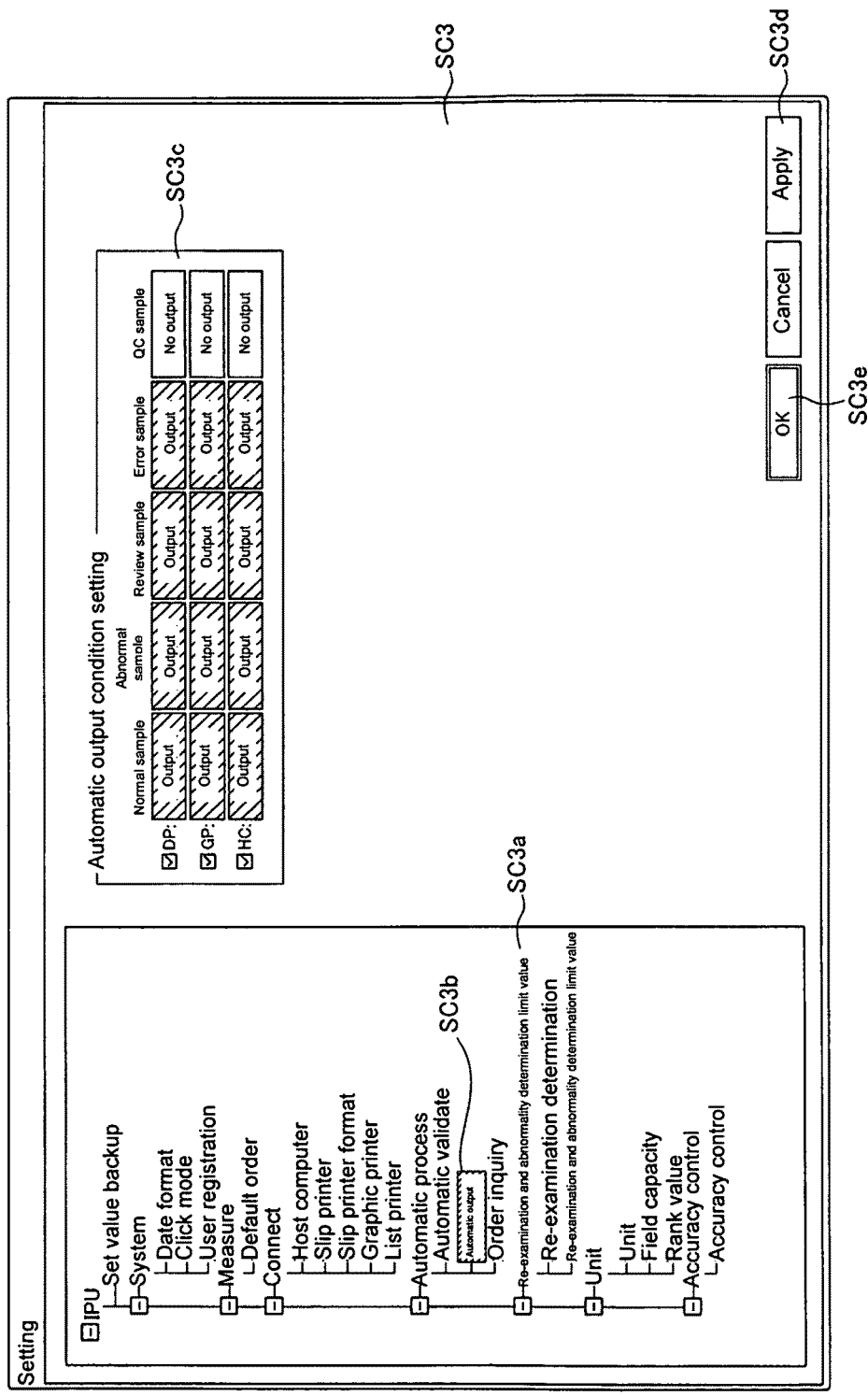
FIG. 7 is a view showing a setting screen of the urine particle analyzer according to one embodiment shown in FIG. 1.

The setting screens SC2 and SC3 shown in FIGS. 6 and 7 are displayed on the display 32 when the user selects a setting icon of the menu screen (not shown).

As shown in FIG. 6, an automatic validation target menu is displayed on a display region SC2c on the right side of a menu tree display region SC2a when the user selects an automatic validate item SC2b of the menu tree display region SC2a. In the automatic validation target menu, the user can select three targets of "no automatic validation", "all samples", and "normal sample". If the user selects "no automatic validation", the user needs to manually validate with respect to all the samples. That is, the setting of the automatic validate function of the urine particle analyzer 1 is invalidated. If "all samples" is selected, the validation is automatically performed on all the samples by the CPU 31a without the user manually performing the validation. If "normal sample" is selected, automatic validation by the CPU 31a is performed only on the normal samples in which the value of analysis result is within a predetermined range. The automatic validate function is set such that after selecting the automatic validation target, the validation is automatically performed on the selected sample to be automatically validated by pushing an apply button SC2d and an OK button SC2e.

As shown in FIG. 7, an automatic output condition setting menu is displayed on the display region SC3c when the user selects an automatic output item SC3b of a menu tree display region SC3a. In the automatic output condition setting menu, three output destinations of "DP (slip printer 50)", "GP (graphic printer 60)", and "HC (host computer 40)" can be selected, and the type of samples to be output to the respective output destination can be selected. Specifically, there are five types of samples for the types of sample including normal sample, abnormal sample, REVIEW sample, ERROR sample, and QC (Quality Control) sample, where whether or not to output to the three output destinations can be selected for the five types of samples. The abnormal sample is a sample indicating an abnormal value in which the value of the analysis result is not within the predetermined range, and the REVIEW sample is a sample in which re-examination by the laboratory technician is desirable. The ERROR sample is a sample in which error occurred during the analysis, and the QC sample is a sample to use for accuracy control of the urine particle analyzer 1. The automatic output function is set such that after the output destination and the type of sample to be output are selected, the analysis result of the selected type of sample is output to the selected output destination by pushing an apply button SC3d and an OK button SC3e. In the present embodiment, the user can validate the automatic output function only when the automatic validate function is valid.

Figure 8:
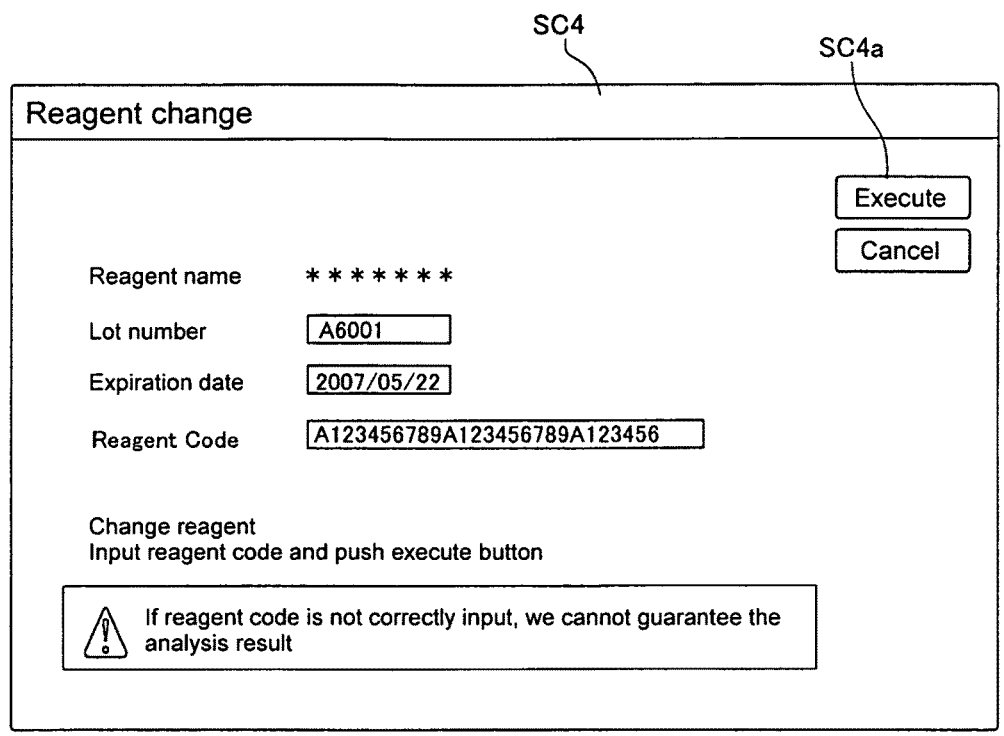
FIG. 8 is a view showing a reagent change screen of the urine particle analyzer according to one embodiment shown in FIG. 1.
Figure 9:
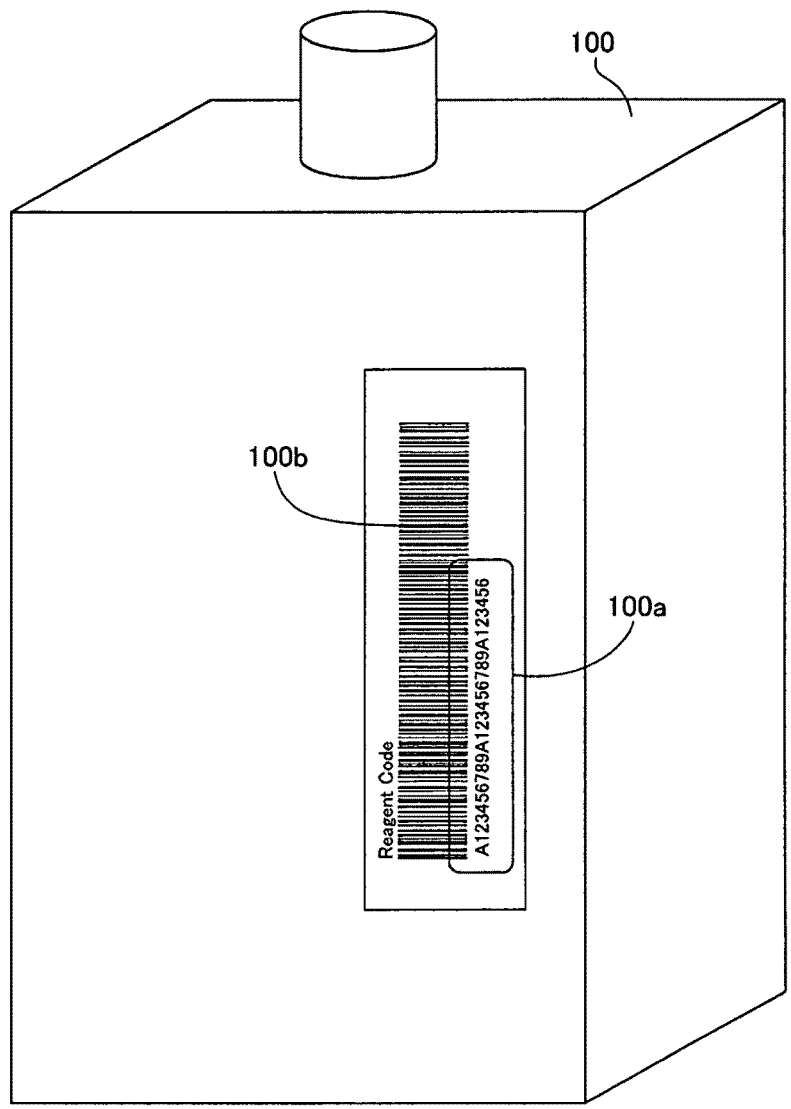
FIG. 9 is a perspective view showing a reagent container used in the urine particle analyzer according to one embodiment shown in FIG. 1.

When the reagent to be used in the measurement section 2 is changed by the user, the CPU 31a outputs a image signal to the image output interface 31g to display a reagent change screen SC4 shown in FIG. 8 on the display 32. The reagent change screen SC4 is configured so that the user can input a twenty-seven digit unique reagent code 100a (see FIG. 9) given to the reagent container 100 (see FIG. 9). The urine particle analyzer 1 can input the reagent code 100a by reading a barcode 100b displayed on the upper part of the reagent code 100a (see FIG. 9) using a barcode reader (not shown). The reagent code is a twenty-seven encrypted digit reagent code storing information unique to a dedicated reagent (genuine product) suited for the measurement by the measurement section 2 such as expiration date, lot number for enabling traceability, and the like. The reagent code 100a is encrypted using the hash function such as MD (Message digest Algorithm) 5. Whether or not the reagent is a dedicated reagent (genuine product) suited for use in the measurement section 2 can be determined based on the encrypted twenty-seven digit alpha-numerals by the CPU 31a. In the present embodiment, the genuine product is the reagent manufactured by the manufacturer of the analyzer or a third party validated by the manufacturer, and is a reagent approved by the manufacturer to be used in the analyzer.

In changing the reagent, the CPU 31a measures the remaining quantity of the reagent in use, and stores the information on the remaining quantity in the RAM 31c along with the reagent code 100a of the relevant reagent. In the RAM 31c, the reagent code of the plurality of reagents used in the past and the information on the remaining quantity are stored as reagent change history. The CPU 31a determines whether or not the changed new reagent is a dedicated reagent (genuine product) based on both the reagent code 100a and the remaining quantity information.

The CPU 31a can update so that the flags J1 and J2 are in the ON state or in the OFF state. The flags J1 and J2 are switched between the ON state and the OFF state when the automatic validate function and the automatic output function are invalidated due to use of non-dedicated reagent (non-genuine product). The flags J1 and J2 are respectively stored in the RAM 31c.

The RAM 31c is configured by SRAM or DRAM. The RAM 31c is used to read out the computer program recorded in the ROM 31b and the hard disc 31d. The RAM 31a is used as a work region of the CPU 31a when executing such computer programs.

The hard disc 31d is installed with various computer programs for the CPU 301a to execute such as operating system and application program, and data used in execution of the computer programs. The application program 34a to be hereinafter described is also installed in the hard disc 31d.

The read-out device 31e is configured by flexible disc drive, CD-ROM drive, DVD-ROM, or the like, and reads computer program or data recorded on a portable recording medium 34. The application program 34a for the computer to realize a predetermined function is stored in the portable recording medium 34, and the computer serving as the data processing section 3 is able to read out the application program 34a from the portable recording medium 34 and install the application program 34a in the hard disc 31d.

The application program 34a is not only provided by the portable recording medium 34, but also provided through the electric telecommunication line (wired or wireless) from the external equipment communicably connected to the data processing section 3 by the electric telecommunication line. For instance, the application program 34a may be stored in the hard disc of the server computer on the Internet, and the data processing section 3 may access the server computer to download the application program 34a and install the same in the hard disc 31d.

The operating system that provides graphical user interface environment such as Windows (Registered trademark) manufactured and sold by US Microsoft Co., Ltd. is installed in the hard disc 31d. In the following description, the application program 34a according to the present embodiment operates on the operating system.

The input/output interface 31f is configured by serial interface such as USB, IEEE1394, RS-232C; parallel interface such as SCSI, IDE, IEEE1284; analog interface including D/A converter, A/D converter and the like. The input device 33 including keyboard and mouse is connected to the input/output interface 31f, so that the data can be input to the data processing section 3 when the user uses the input device 33. The input device 33 also has a function of accepting measurement value data. The input/output interface 31f can output the analysis result to the slip printer 50 and the graphic printer 60.

The communication interface 31i is the Ethernet (registered trademark) interface, and the data processing section 3 can transmit and receive data with the measurement section 2 connected by LAN cable by using a predetermined communication protocol (TCP/IP) by means of the communication interface 31i. A host computer 40 is connected to the communication interface 31i, and the communication interface 31i can transmit (output) analysis result to the host computer 40.

The image output interface 31g is connected to the display 32 configured by LCD, CRT, or the like, and outputs an image signal provided from the CPU 31a to the display 32. The display 32 displays the image (screen) according to the input image signal.

Figure 10:
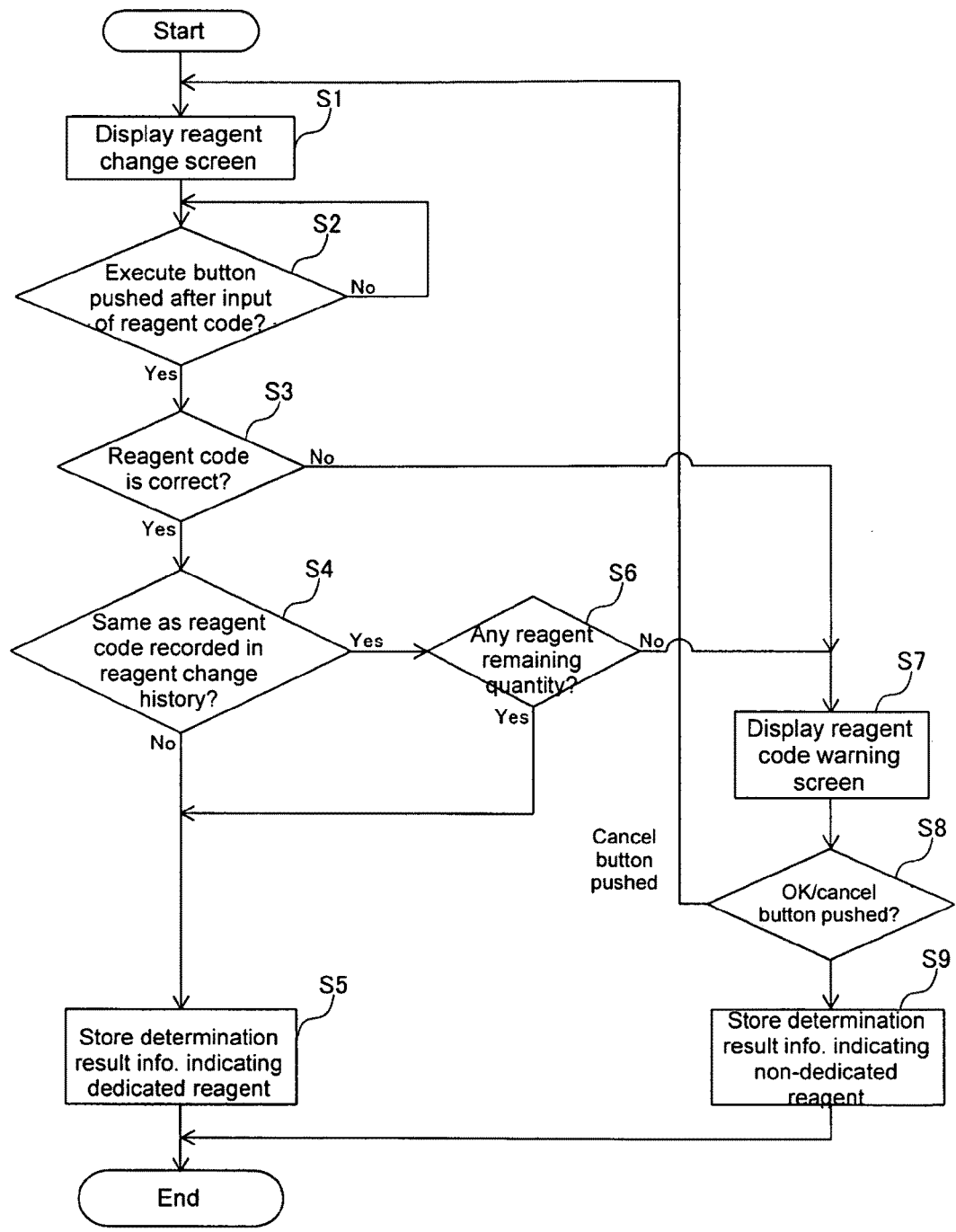
FIG. 10 is a flowchart describing an operation of determining whether or not the changed reagent is a dedicated reagent (genuine product) in the urine particle analyzer according to one embodiment of the present invention.
Figure 11:
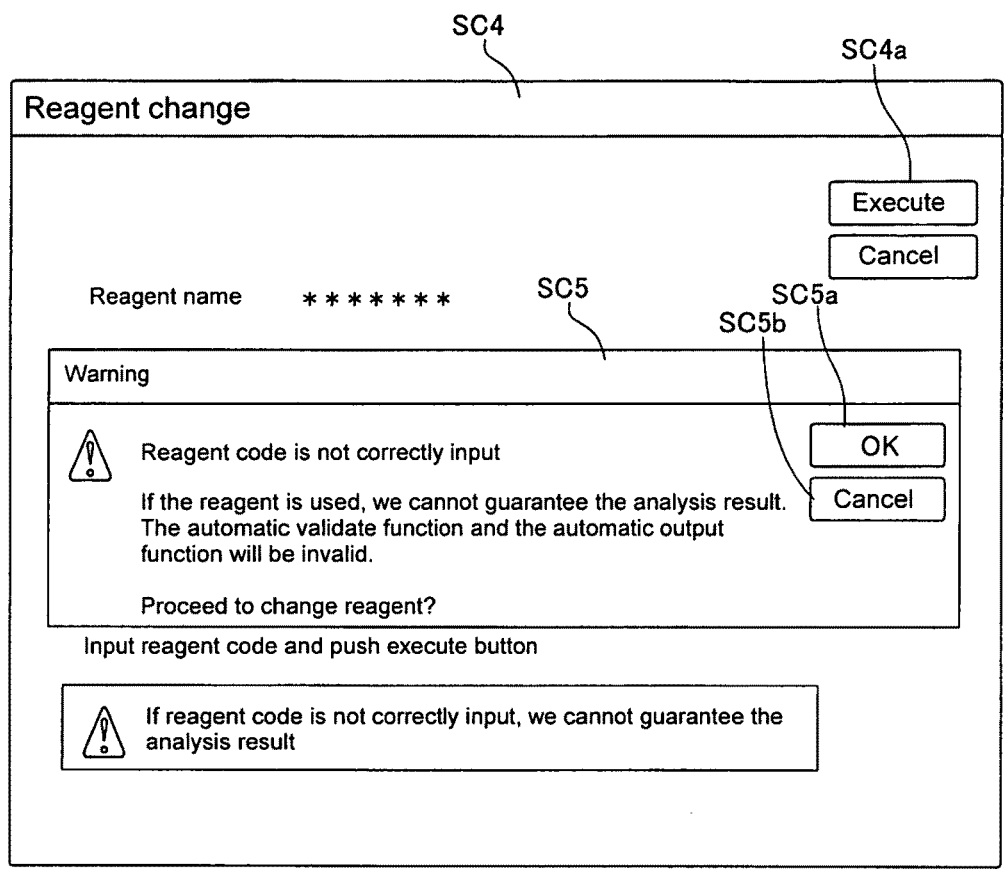
FIG. 11 is a view showing a reagent code warning screen of the urine particle analyzer according to one embodiment shown in FIG. 1.

FIG. 10 is a flowchart describing an operation of determining whether or not the changed reagent is a dedicated reagent (genuine product) in the urine particle analyzer according to one embodiment of the present invention. FIG. 11 is a view showing a reagent code warning screen of the urine particle analyzer according to one embodiment shown in FIG. 1. With reference to FIGS. 8 to 11, the genuine product determining operation of determining whether or not the changed reagent is a dedicated reagent (genuine product) in the urine particle analyzer 1 according to one embodiment of the present invention will be described.

First, in step S1 of FIG. 10, the reagent change screen SC4 shown in FIG. 8 is displayed, and the input of the reagent code is urged to the user. The reagent change screen SC4 is displayed on the display 32 by having the user double click the reagent change icon on the menu screen (not shown). In step S2, whether or not the user has input the twenty-seven digit reagent code 100a (see FIG. 9) given to the reagent in the reagent change screen SC4, and pushed the execute button SC4a is determined. If the execute button SC4a is not pushed, this determination is repeated. If the execute button SC4a is pushed, whether or not the input reagent code is correct is determined in step S3. Specifically, whether or not it is the twenty-seven digit alpha-numerals correctly created according to the algorithm of MD5 used in encryption. That is, whether or not the condition for determining whether the changed reagent is a genuine product is satisfied is determined. In this step, it is checked if the reagent code given to the reagent is at least the reagent code of the genuine product. If the input reagent code is correct, the lot number and the expiration date encrypted and stored in the twenty-seven digit alpha-numerals are decrypted, and displayed in each filed of the reagent change screen SC4. If the input reagent code is correct, the operation proceeds to step S4.

If the reagent code is incorrect, the reagent code warning screen SC5 as shown in FIG. 11 is displayed in step S7. In the reagent code warning screen SC5, warning that the reagent codes is not correctly input, that the automatic validate function and the automatic output function are not working, and that there is not guarantee in the analysis result is displayed.

A display for confirming the user on the decision whether or not the execute the reagent change is made. This is due to the following reasons. The dedicated reagent is optimized for the urine particle analyzer in respect of the components and the like such that high accuracy analysis result is obtained in the urine particle analyzer. In the urine particle analyzer according to the present embodiment, the evaluation experiment is repeatedly performed and the urine particle analyzer is designed so that high accuracy analysis result is guaranteed when analysis is performed using the dedicated reagent (genuine reagent). Therefore, when the sample is analyzed in the urine particle analyzer using the reagent (non-dedicated reagent) other than the dedicated reagent which performance is guaranteed by the supplier of the urine particle analyzer according to the present embodiment, there is not guarantee that an accurate analysis result will be obtained, and the reliability of the analysis result lowers.

In step S8, whether or not one of the buttons of the OK button SC5a or the cancel button SC5b of the reagent code warning screen SC5 is pushed is determined, where the process proceeds to step S1 if the cancel button SC5b is pushed. If the OK button SC5a is pushed, the determination result information indicating the non-dedicated reagent (non-genuine product) is stored in the RAM 31c and the operation is terminated in step S9.

If the reagent code is correct, whether or not the reagent code same as the input reagent code exists in the reagent codes of a plurality of reagents used in the past which are stored in the RAM 31c as reagent change history is determined in step S4. If the same reagent code does not exist, the determination result information indicating the dedicated reagent (genuine product) is stored in the RAM 31c in step S5 and the operation is terminated.

If the input reagent code is the same as one of the reagent codes of a plurality of reagents stored in the RAM 31c, the information on the remaining quantity of the reagent stored with the reagent code in the RAM is checked in step S6. Thus, if stored in the RAM 31c that there is no remaining quantity of the reagent corresponding to the input reagent code, this means that all the reagents have already been used and changed, and determination may be made that the non-dedicated reagent is used as a dedicated reagent, for example, another reagent (non-genuine product) is refilled and used in the container of the reagent to be changed, or the reagent code given to the dedicated reagent (non-genuine product) used in the past is input and the changed reagent is a non-genuine product. That is, in this step as well, whether or not the condition for determining whether the changed reagent is a genuine product is satisfied is determined. Therefore, if there is no reagent remaining quantity stored in the RAM 31c in step S6, the process proceeds to step S7, and the reagent code warning screen SC5 is displayed. If there is reagent remaining quantity, the process proceeds to step S5 assuming it is the dedicated reagent (genuine product). Thus, by performing the genuine product determining operation before changing the reagent, a state in which the changed reagent is used for measurement and analysis with whether the reagent is a dedicated reagent (genuine product) being unclear is suppressed.

Figure 12:
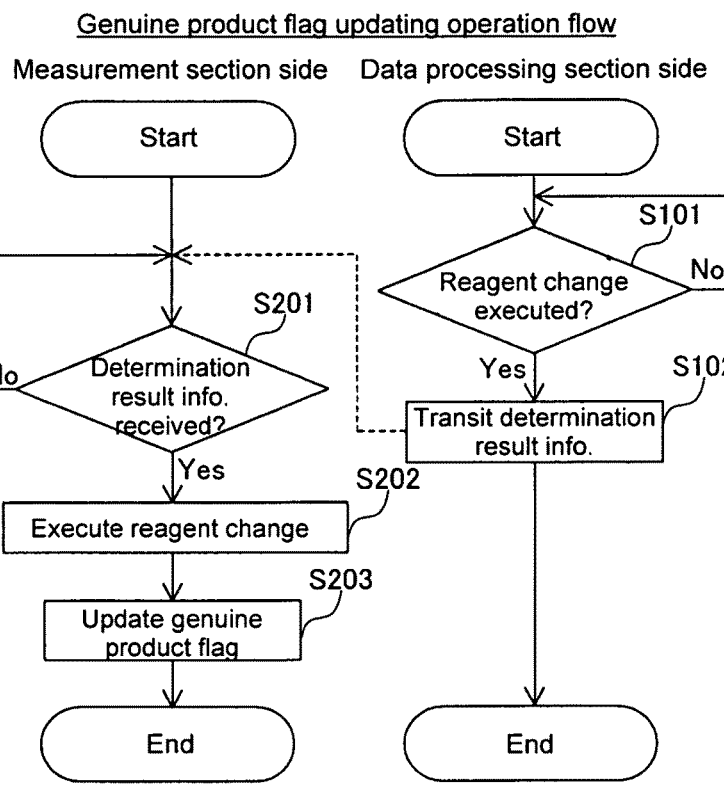
FIG. 12 is a flowchart describing an operation of updating the information whether genuine product or not in the urine particle analyzer according to one embodiment of the present invention.

FIG. 12 is a flowchart describing the operation of updating the information on whether genuine product or not in the urine particle analyzer according to one embodiment of the present invention. The genuine product flag updating operation of updating the information on whether genuine product or not in the urine particle analyzer 1 according to one embodiment of the present invention will be described with reference to FIG. 10 and FIG. 12.

In step S101 of FIG. 12, whether or not the change of reagent is executed is determined on the data processing section 3 side, where if it is not executed, the determination is repeated. Specifically, whether or not the change of reagent is executed is determined based on whether or not the genuine product determining operation of the flowchart shown in FIG. 10 is terminated. If terminated, this means that the change of reagent is executed, and thus the signal of the determination result information is transmitted to the measurement section 2 in step S102 and the operation is terminated.

On the measurement section 2 side, in step S201, the signal of the determination result information transmitted from the data processing section 3 is received. In step S202, the sequence control in the reagent change is executed. The sequence control in the reagent change is the preparation operation for performing the measurement of the next time. Specifically described, when the reagent change is performed, air may enter the tube for flowing the reagent, or the reagent may not exist in the space in the tube in which the reagent is to originally exist. In the sequence control in the reagent change, the reagent is aspirated from the newly set reagent container, and the reagent is filled in the tube. In step S203, information on whether or not the dedicated reagent (genuine product) is stored in the memory 27 based on the signal of the received determination result information. Specifically, in the case of the dedicated reagent (genuine product), update is performed such that the genuine product flag stored in the memory 27 is turned ON, and in the case of the non-dedicated reagent (non-genuine product), update is performed such that the genuine product flag is turned OFF. Thereafter, the operation of the measurement section 2 is terminated.

Figure 13:
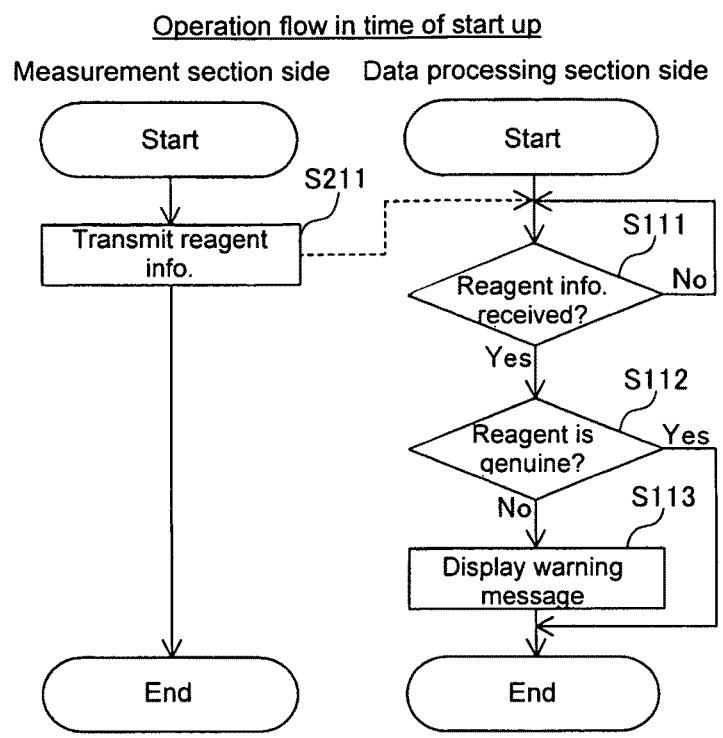
FIG. 13 is a flowchart describing an operation in time of start up of the urine particle analyzer according to one embodiment of the present invention.
Figure 14:
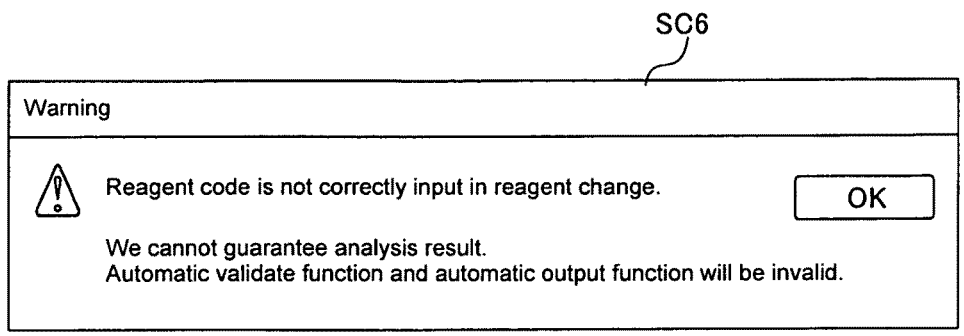
FIG. 14 is a view showing a warning screen of the urine particle analyzer according to one embodiment shown in FIG. 1.

FIG. 13 is a flowchart describing the operation in time of start up of the urine particle analyzer according to one embodiment of the present invention. FIG. 14 is a view showing a warning screen of the urine particle analyzer according to one embodiment shown in FIG. 1. The operation in time of start up of the urine particle analyzer 1 according to one embodiment of the present invention will be described with reference to FIGS. 13 and 14.

First, in step S211 of FIG. 13, the reagent information signal is transmitted to the data processing section 3 based on the state of the genuine product flag stored in the memory 27 of the measurement section 2. Specifically, when the genuine flag is turned ON, a signal notifying that the reagent to be used is the dedicated reagent (genuine product) is transmitted to the data processing section 3, and when the genuine flag is turned OFF, a signal notifying that the reagent to be used is the non-dedicated reagent (non-genuine product) is transmitted, and the operation is terminated.

In the data processing section 3, in step S111, the reagent information signal transmitted from the measurement section 2 is received, and in step S112, whether the dedicated reagent (genuine reagent) or not is checked based on the received reagent information signal. In the case of the dedicated reagent (genuine product), the operation is terminated, and in the case of the non-dedicated reagent (non-genuine product), the warning screen SC6 is displayed as shown in FIG. 14 in step S13. In the warning screen SC6, warning that the reagent code is not correctly input in reagent change, that the analysis result cannot be guaranteed, and that the automatic validate function and the automatic output function do not operate is displayed. Thus, by displaying the warning screen SC6 in time of start up (in time of activation), the user can recognize that the reliability of the analysis result to be obtained is low before the measurement and the analysis are started. Furthermore, the user can recognize that the automatic validate function and the automatic output function are invalidated. Thereafter, the operation of the data processing section 3 is terminated.

Figure 15:
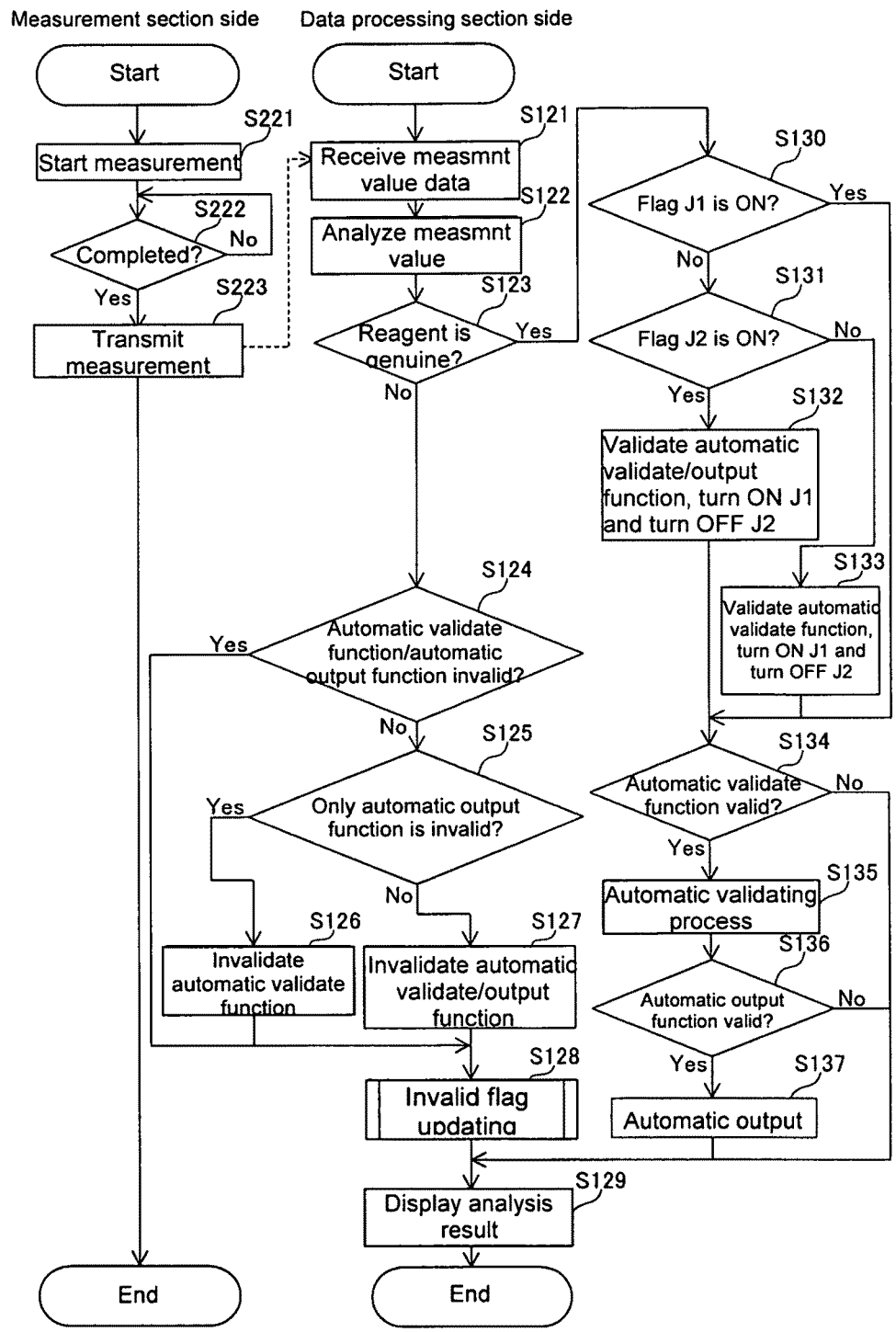
FIG. 15 is a flowchart describing a measurement and analyzing operation of the urine particle analyzer according to one embodiment of the present invention.

FIG. 15 is a flowchart describing the operation of the measurement and the analysis of the urine particle analyzer according to one embodiment of the present invention. The operation of the measurement and the analysis of the urine particle analyzer 1 according to one embodiment of the present invention will be described with reference to FIGS. 5 to 7, FIG. 13, and FIG. 15.

First, the measurement of the particles in the urine is started by the measurement section 2 in step S221 of FIG. 15, and whether or not the measurement is completed is determined in step S222. If the measurement is not completed, the determination is repeated while continuing measurement. If the measurement is completed, the measurement value data is transmitted to the data processing section 3 through the LAN adapter 29 in step S223, and the operation on the measurement section 2 side is terminated.

On the data processing section 3 side, in step S121, the measurement value data transmitted from the measurement section 2 is received, and in step S122, the measurement value is processed (analyzing process) based on the received measurement data. In step S123, whether or not the reagent being used is the dedicated reagent (genuine product) is determined based on the check result of the reagent information signal checked in step S112 of the operation in time of start up shown in FIG. 13.

If determined as the non-dedicated reagent (non-genuine product) in step S123, determination is made on whether or not both the automatic validate function and the automatic output function are set to invalidation so as not to operate in step S124. Specifically, if "no automatic validation" is selected from the automatic validate target menu shown in FIG. 6, and "output" is not selected in any of the automatic output condition setting menu shown in FIG. 7, both the automatic validate function and the automatic output function are set to invalidation, and the operation proceeds to step S128. If neither of them are invalidated, or if either one is invalidated, whether or not only the automatic output function is set to invalidation is determined in step S125. That is, if not even one "output" is selected in the automatic output condition setting menu, and items other than "no automatic validation" are selected from the automatic validate target menu, only the automatic output function is set to invalid, and the process proceeds to step S126. In step S127, since the automatic validate function is set to valid, the automatic validate function is changed to an invalid state by the CPU 31*a* so as not to be automatically validated. If both the automatic validate function and the automatic output function are set to valid by the user, both the automatic validate function and the automatic output function are changed to the invalid state by the CPU 31*a* so that validation and output are not automatically performed in step S127. In this case, the validation and the output of the analysis result are not automatically performed, but the user can push the validate button SC1*d* to validate by hand. The analysis result can be manually output by pushing the output button SC1*f*.

In step S128, an invalid flag updating process operation for storing change of the automatic validate function and the automatic output function, which are made valid by the setting of the user, to invalid by the CPU 31*a* is performed along the invalid flag updating process operation of FIG. 16 to be hereinafter described. In step S129, the analysis result of a state display limited in step S124 is displayed.

If determined as dedicated reagent (genuine product) in step S123, whether or not the flag J1 stored in the RAM 31*c* is turned ON is determined in step S130. Steps S130 to S133 are operations for, as the non-dedicated reagent (non-genuine product) is used in the past, returning at least either one of the automatic validate function and the automatic output function changed to the invalid state by the CPU 31*a* from the valid state or the setting of the user to the original valid state set by the user. If the flag J1 is turned ON, both states of the current automatic validate function and the automatic output state match the setting state set by the user. That is, both the automatic validate function and the automatic output function are not changed to the invalid state by the CPU 31*a*. If determined that the flag J1 is turned ON in step S130, there is no need to return to the original state set by the user, and thus the process proceeds to step S134.

If the flag J1 is not turned ON, whether or not the flag J2 is turned ON is determined in step S131. If the flag J2 is turned ON, both the automatic validate function and the automatic output function are in a state in which the valid setting of the setting of the user is changed to the invalid state by the CPU 31. If the flag J2 is turned ON, the invalid state of both the automatic valid function and the automatic output function is canceled so that both validation and output can be automatically performed in step S132. The update is performed so that the flag J1 of the RAM 31*c* is turned ON and the flag J2 is turned OFF. The default value of the flags J1 and J2 is J1 is ON and J2 is OFF. Therefore, the flags J1 and J2 are respectively returned to the default values in step S132. The process proceeds to step S133 if the flag J2 is not in the ON state. If the flag J1 is not in the ON state and the flag J2 is also not in the ON state, both flags J1 and J2 are in the OFF state, which a state in which only the automatic validate function is changed to the invalid state by the CPU 31*a* although the setting by the user is valid. Therefore, in step S133, the invalid state of the automatic validate function is canceled so that validation is automatically performed, and update is performed such that the flag J1 is in the ON state and the flag J2 is in the OFF state.

After processing so that both states of the automatic validate function and the automatic output function match the setting state set by the user in steps S130 to S133, whether or not the setting state of the automatic validate function set by the user is valid is determined in step S134. If not valid, the analysis result screen SC1 as shown in FIG. 5 is displayed in step S129, and the operation is terminated.

When the automatic validate function is effective, the automatic validation process is performed on the sample of automatic validate target selected by the user in step S135. In step S136, whether or not the automatic output function is effective is determined, where the process proceeds to step S129 if not effective. When the automatic output function is effective, the automatic output process is performed based on the automatic output condition set by the user in step S137, and the process proceeds to step S129.

Figure 16:
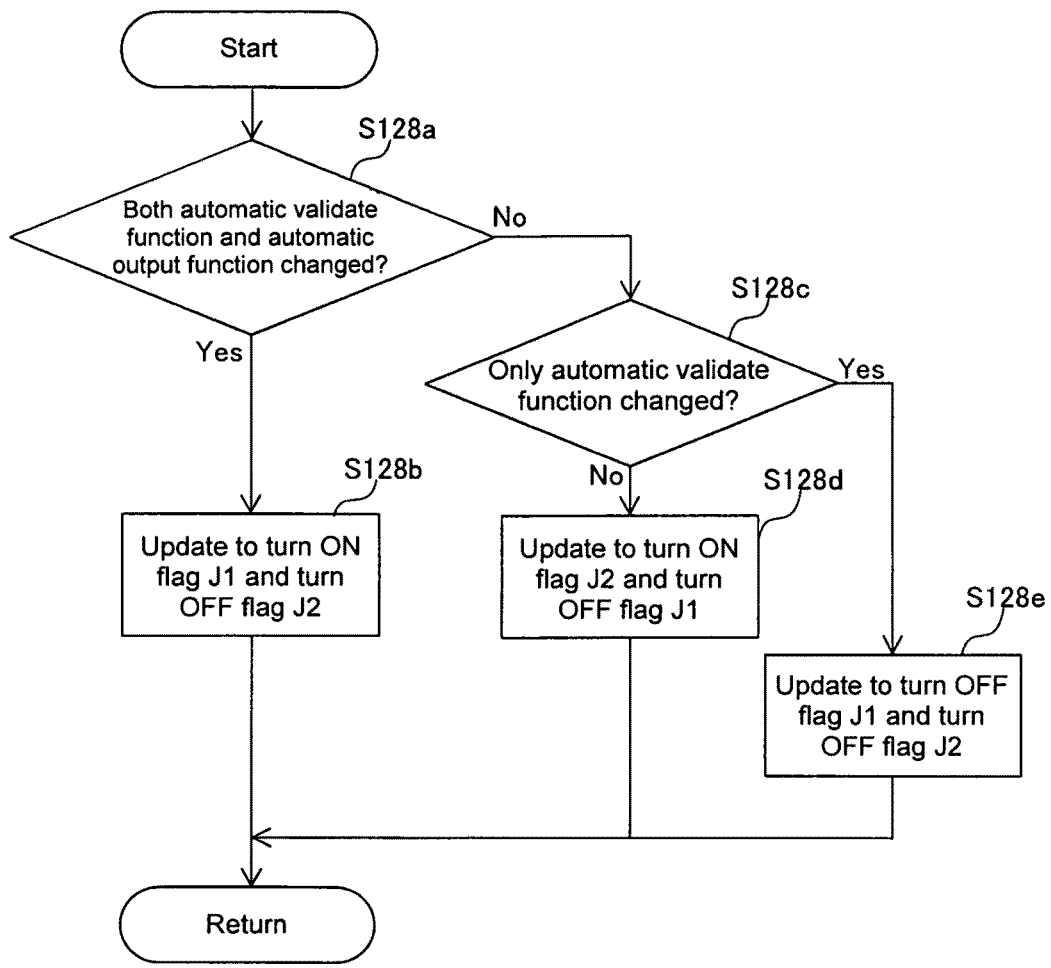
FIG. 16 is a flowchart describing the operation of an invalid flag updating process in step S128 of the measurement and analyzing operation shown in FIG. 15.

FIG. 16 is a flowchart describing the operation of the invalid flag updating process in step S128 of the measurement and analyzing operation shown in FIG. 15. The invalid flag updating process operation in step S128 of the measurement and analyzing operation shown in FIG. 15 will be described with reference to FIGS. 15 and 16.

First, in step S128*a*, whether or not change is made to the invalid state by the CPU 31*a* although the setting by the user is valid is determined for both the automatic validate function and the automatic output function. If both are changed, update is performed so that the flag J1 is turned ON and update is performed so that the flag J2 is turned OFF in step S128*b*. Thereafter, the operation is terminated. If at least one of the automatic validate function or the automatic output function is changed, determination is made on whether only the automatic validate function is changed in step S128c. When only the automatic validate function, update is performed such that both flags J1 and J2 are turned OFF in step S128e, and the operation is terminated. If both the automatic validate function and the automatic output function are changed, update is performed such that the flag J2 is turned ON and update is performed such that the flag J1 is turned OFF in step S128d. Subsequently, the process returns to step S129 of the measurement and analyzing operation flow.

In the present embodiment, as described above, the CPU 31a executes the application program 34a to determine whether or not the reagent is appropriate for the measurement of the sample by the measurement section 2 based on the reagent code 100a received by the reagent change screen SC4. The function is limited so that validation of the analysis result is not automatically performed when determined that the reagent is not appropriate for the measurement of the sample by the measurement section 2. The analysis result of low reliability due to non-dedicated reagent (non-genuine product) not appropriate for the measurement is prevented from being automatically validated.

In the present embodiment, the CPU 31a executes the application program 34a to enable the analysis result to be automatically output, and limit the function so that the analysis result is not automatically output when determined that the reagent is not appropriate for the measurement of the sample by the measurement section 2. According to such configuration, the analysis result of low reliability is prevented from being automatically output.

Second Embodiment

A urine particle analyzer according to a second embodiment of the present invention will now be described based on the drawings. The hardware of the urine particle analyzer has a hardware configuration shown in FIGS. 1, 2, 3, and 4, similar to the urine particle analyzer according to the first embodiment, and thus the detailed description of the hardware configuration will be omitted. Furthermore, unless particularly stated, the urine particle analyzer of the second embodiment is an analyzer having functions similar to the urine particle analyzer of the first embodiment. Description will be made using same reference numerals for the configurations common with the first embodiment.

In the present embodiment, the CPU 31a has a function of obtaining the analysis result by processing the measurement value measured by the measurement section 2, and outputting an image signal corresponding to analysis result screens SC7 to SC12 (see FIGS. 18 to 23) for displaying the analysis result to the image output interface 31g. The analysis result screen SC7 includes a display region SC7a for displaying numerical data on the basic items, a display region SC7b for displaying numerical data on the research items, and a display region SC7c for displaying a scattergram indicating the distribution of number, size, and the like of particles in the measurement specimen in the basic item. The basic items are highly important measurement items used in diagnosis, and the research items are auxiliary measurement items of lower importance than the basic items used as a reference of the diagnosis. In the analysis result screen SC7, the analysis results of RBC (red blood cells), WBC (white blood cells), EC (epidermal cells), CAST (casts), and BACT (bacteria) are shown as basic items, and analysis results of X'TAL (crystal), YLC (yeast-like fungus), SRC (small round cells), Path. CAST (diseased cast including cell component), MUCUS (thread of mucus), SPERM (sperm), and Cond. (urine conductivity) are shown as research items.

As shown in FIG. 19, an asterisk display (*) of the display region SC8a of the analysis result screen SC8 is given to the measurement items to be desirably re-examined by the laboratory technician as a result of processing the measurement value by the data processing section 3. The asterisk display is also given when the reliability of the analysis result is low. The review display of the display region SC8b is displayed in red to stand out near the upper left of the analysis result screen SC8 so that the user can easily recognize that the sample is desirably re-examined when the asterisk display is given.

Figure 20:
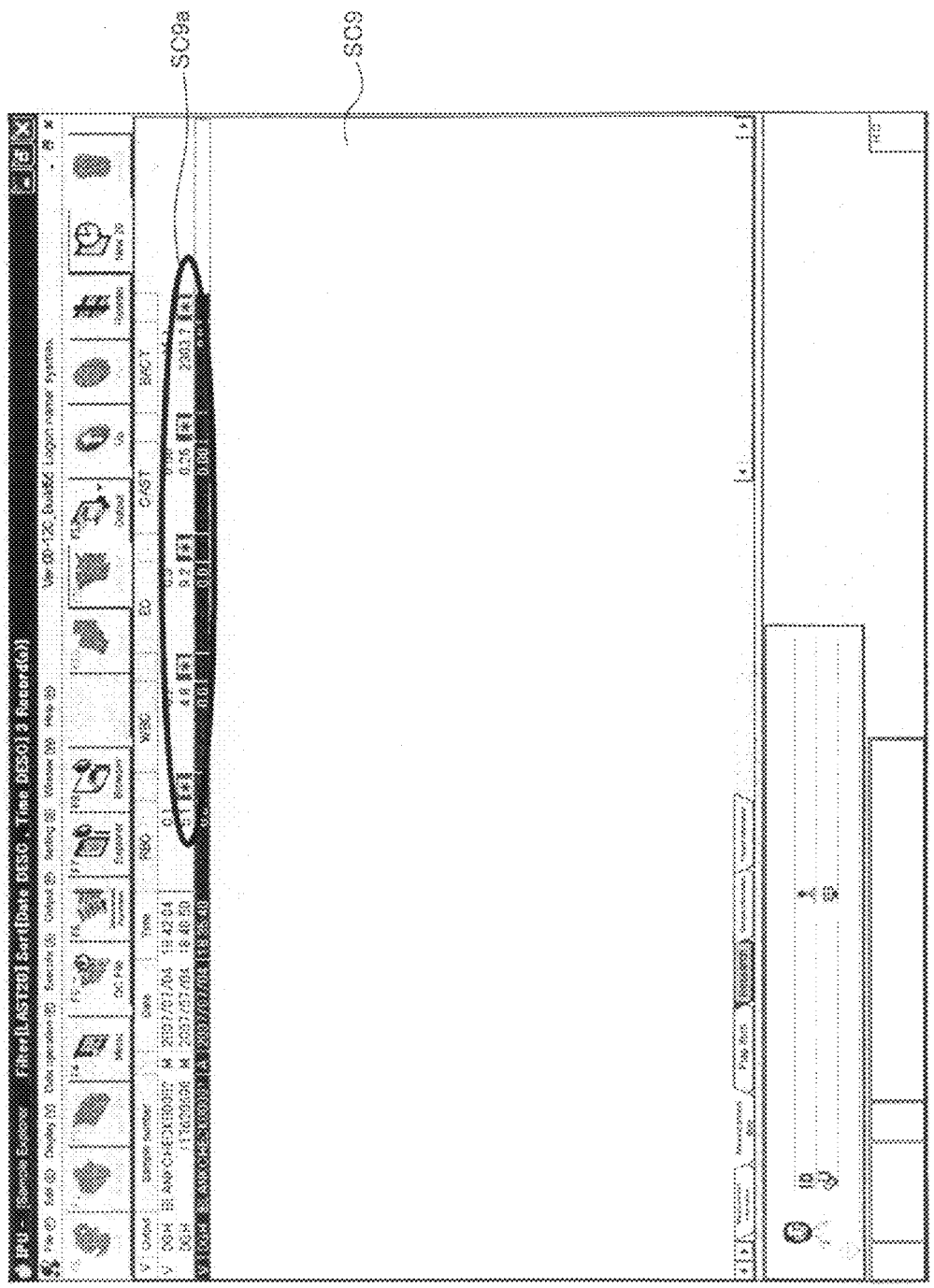
FIG. 20 is a view showing an analysis result screen of the urine particle analyzer according to one embodiment shown in FIG. 1.
Figure 21:
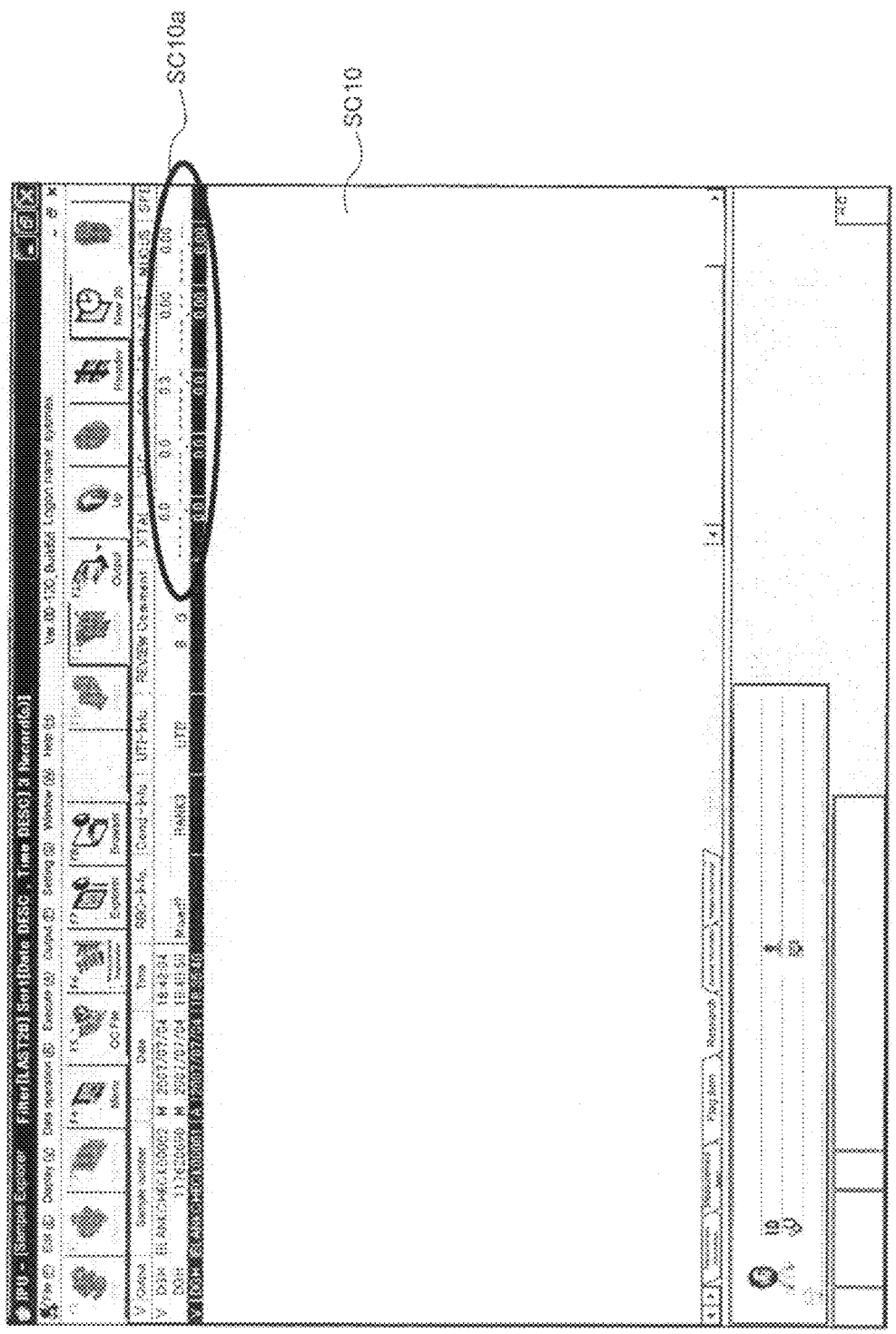
FIG. 21 is a view showing an analysis result screen of the urine particle analyzer according to one embodiment shown in FIG. 1.
Figure 22:
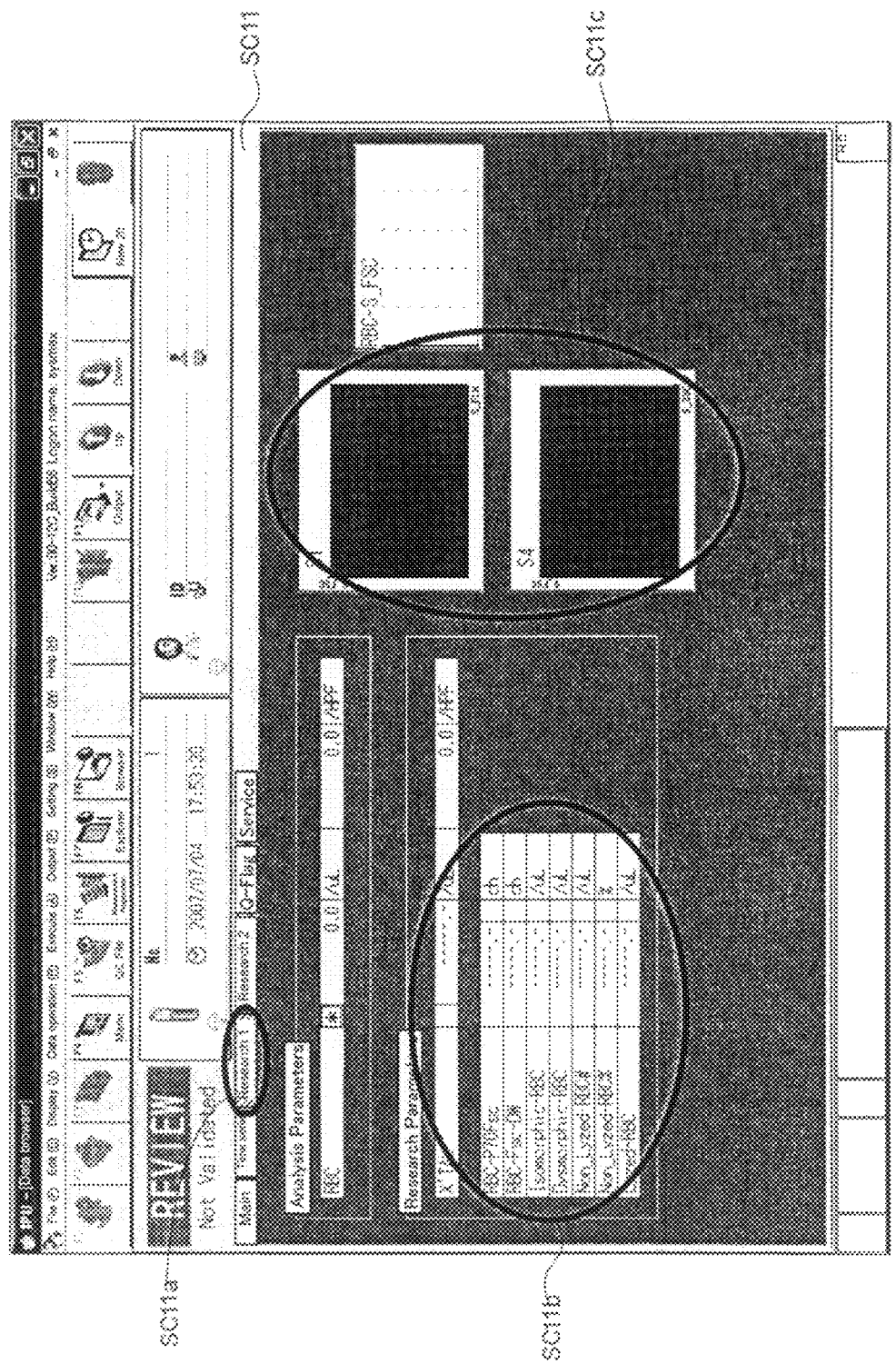
FIG. 22 is a view showing an analysis result screen of the urine particle analyzer according to one embodiment shown in FIG. 1.
Figure 23:
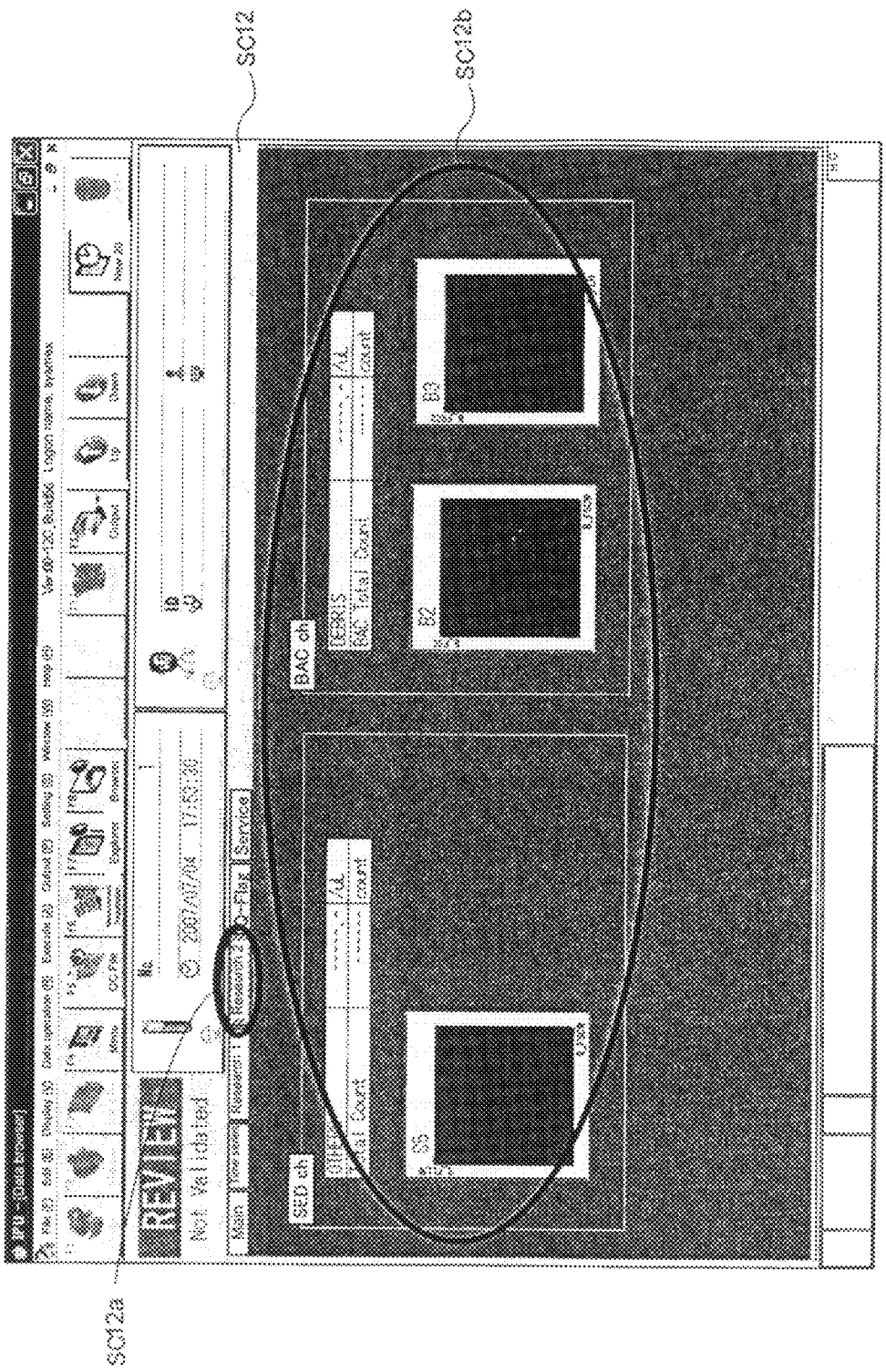
FIG. 23 is a view showing an analysis result screen of the urine particle analyzer according to one embodiment shown in FIG. 1.

The analysis result screen SC9 shown in FIG. 20 is a screen for displaying a list of analysis results for the basic items of the plurality of samples. The asterisk display of the display region SC9a in the analysis result screen SC9 is given to the measurement item to be desirably re-examined by the laboratory technician, similar to the above. The analysis result screen SC10 shown in FIG. 21 is a screen for displaying a list of analysis results for the research items of the plurality of samples. The analysis result screen SC11 shown in FIG. 22 is a screen for displaying red blood cell form information as the research item. The analysis result screen SC12 shown in FIG. 23 is a screen for displaying urine concentration information and the like as the research item.

In the present embodiment, the displaying process of the reagent change screen SC4 (FIG. 8) of when the user changes the reagent to be used in the measurement section 2, and the input of the reagent code 100a using the barcode reader are performed similar to the first embodiment. Similar to the first embodiment, the CPU 31a measures the remaining quantity of the reagent being used. Therefore, whether or not the reagent is the dedicated reagent (genuine product) appropriate for use in the measurement section 2 can be determined by the CPU 31a. The CPU 31a determines whether or not the changed new reagent is the dedicated reagent (genuine product) based on both the reagent code 100a and the remaining quantity information. In the present embodiment as well, the genuine product is the reagent manufactured by the manufacturer of the analyzer or a third party validated by the manufacturer, and is a reagent approved by the manufacturer to be used in the analyzer, similar to the first embodiment.

The flow of determining whether or not the changed reagent is the dedicated reagent (genuine product) is similar to the first embodiment, and is as described using FIGS. 10 and 11. The genuine product flag updating operation for updating the information on whether or not the reagent being used is a genuine product is similar to the first embodiment, and is as described using FIGS. 10 and 12. The operation in time of start up is also similar to the first embodiment, and is as described using FIGS. 13 and 14.

Figure 24:
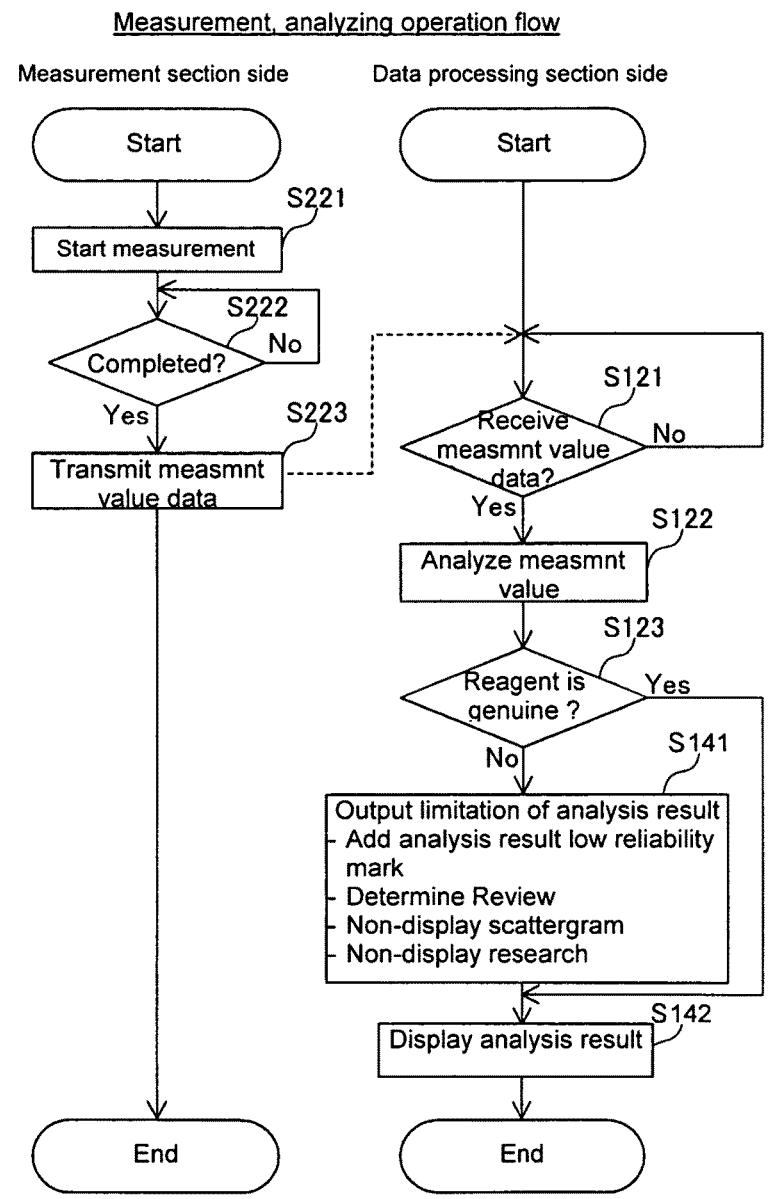
FIG. 24 is a flowchart describing the measurement and analyzing operation of the urine particle analyzer according to one embodiment of the present invention.

FIG. 24 is a flowchart describing the operation of the measurement and the analysis of the urine particle analyzer according to the second embodiment of the present invention. The operation of the measurement and the analysis of the urine particle analyzer 1 according to the second embodiment of the present invention will be described with reference to FIGS. 18 to 23, 13 and 24. In the flowchart of FIG. 24, same reference numerals are used for steps common with the flowchart of FIG. 15 used in the description of the first example.

First, in step S221 of FIG. 24, the measurement of the particles in the urine is started by the measurement section 2, and whether or not the measurement is completed is determined in step S222. If the measurement is not completed, the determination is repeated while continuing measurement. If the measurement is completed, the measurement value data is transmitted to the data processing section 3 through the LAN adapter 29 in step S223, and the operation on the measurement section 2 side is terminated.

On the data processing section 3 side, in step S121, the measurement value data transmitted from the measurement section 2 is received, and in step S122, the measurement value is processed (analyzing process) based on the received measurement data. In step S123, whether or not the reagent being used is the dedicated reagent (genuine product) is determined based on the check result of the reagent information signal checked in step S112 of the operation in time of start up shown in FIG. 13.

Figure 18:
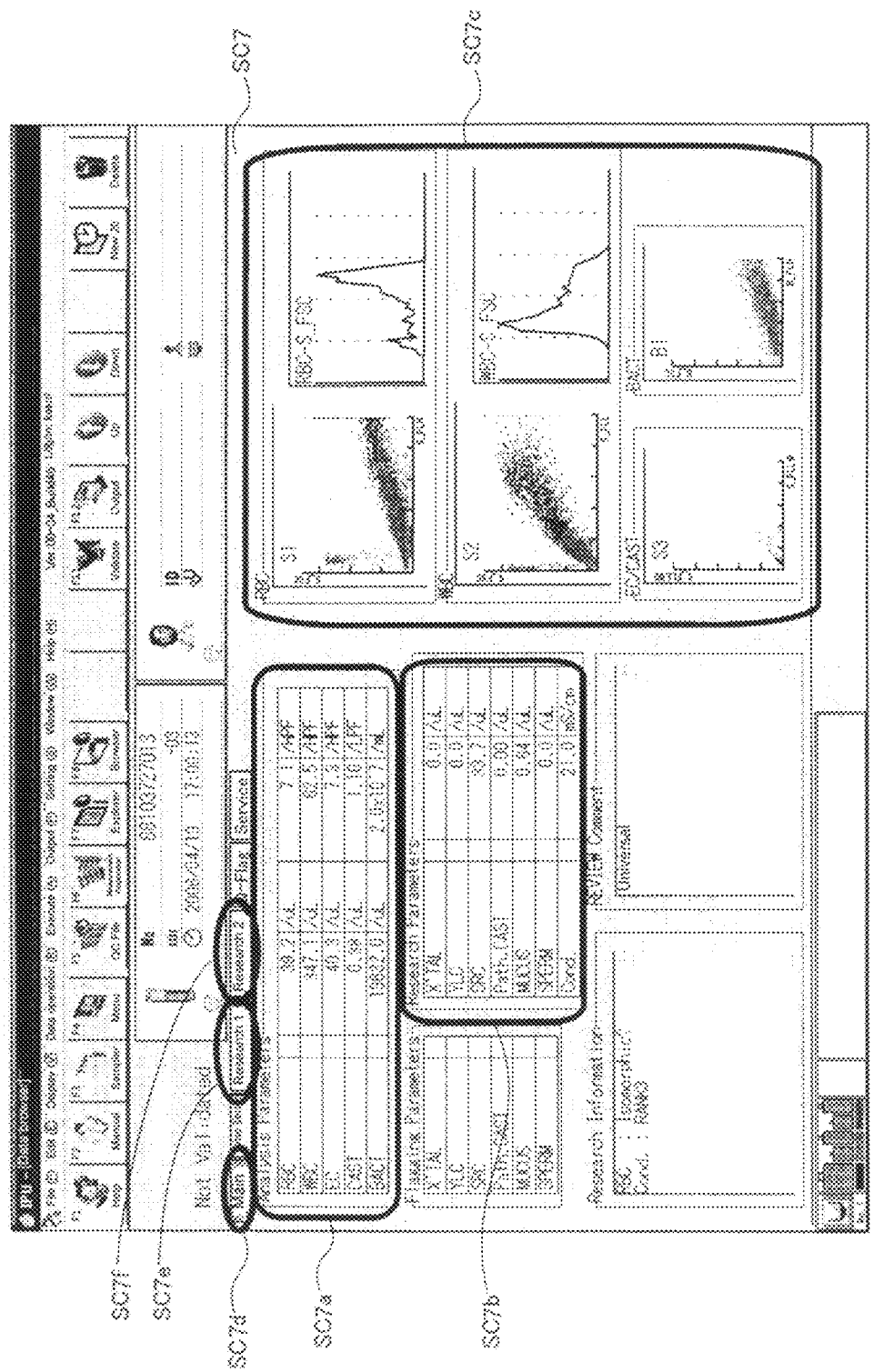
FIG. 18 is a view showing an analysis result screen of the urine particle analyzer according to one embodiment shown in FIG. 1.
Figure 13:
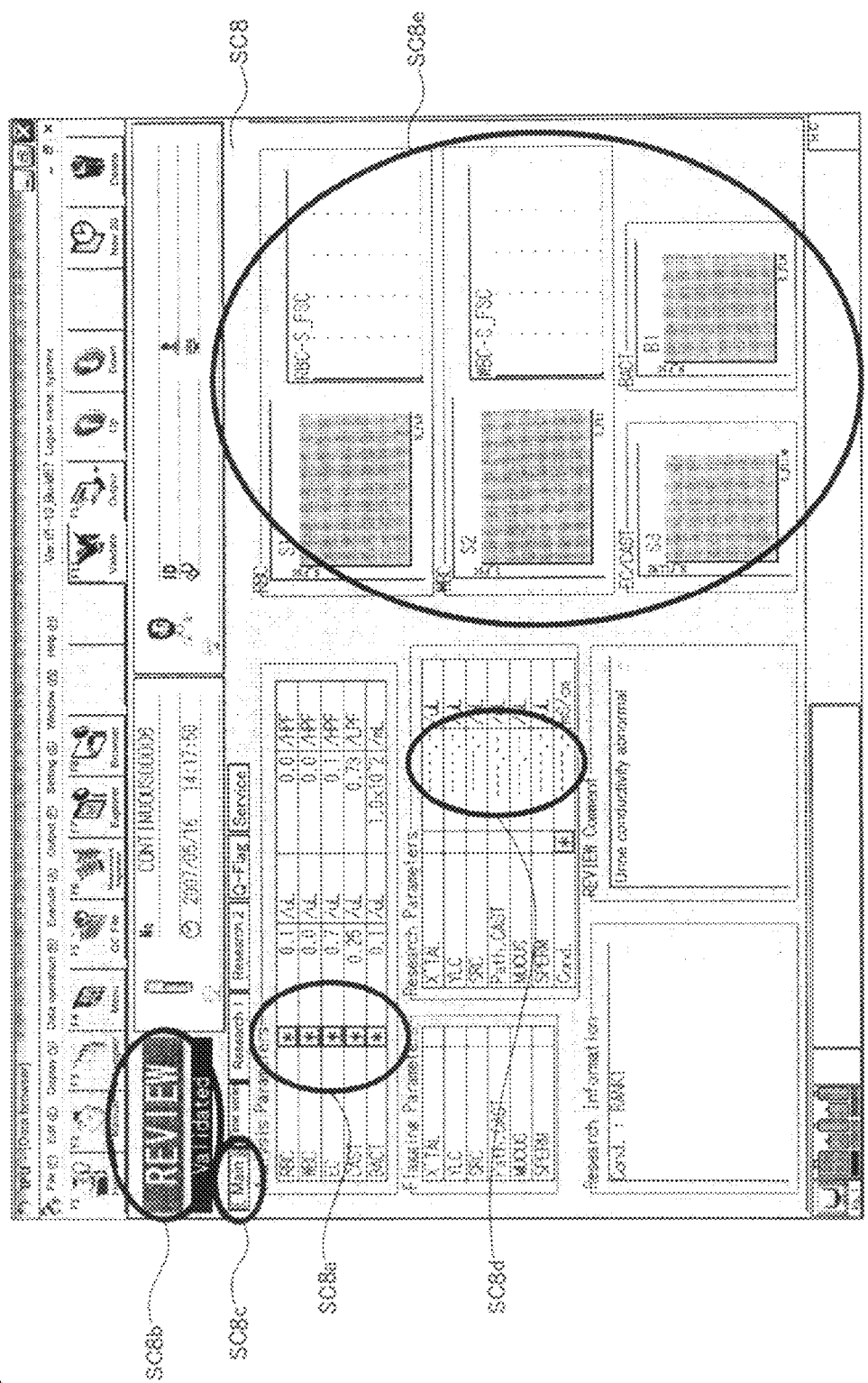

In the present embodiment, if determined as the dedicated reagent (genuine product) in step S123, the analysis result screen SC7 as shown in FIG. 18 is displayed in step S142. The analysis result screen SC7 is the display of the state in which the main tab SC7d is selected, and the analysis results of all of the numerical data for the basic items of the display region SC7a, the numerical data for the research items of the display region SC7b, and the scattergram of the display region SC7c are displayed. In other words, when the dedicated reagent (genuine product) is used, all of the analysis results of the basic items and the research items that can be analyzed in the urine particle analyzer 1 are displayed. All the analysis results are also displayed when the research 1 tab SC7e and the research 2 tab SC7f are selected.

In step S123, when determined as the non-dedicated reagent (non-genuine product), the output limitation of the analysis result is made in step S141. Specifically, as shown in FIG. 19, the asterisk display (*) of the display region SC8a is given to the field of all the basic items in the analysis result screen SC8 in a state the main tab SC8c is selected. The measurement is conducted with the non-dedicated reagent (non-genuine product), and thus the reliability of the analysis result is low, and re-examination by the laboratory technician is desirable. The review display of the display region SC8n is also given by giving the asterisk display. Since the reliability of the analysis result is low, the numerical data on the research items of the display region SC8d of low importance are all non-displayed by a hyphen sign (-). The scattergram of the display region SC8e is also non-displayed. In the analysis result screen SC9 shown in FIG. 20, the asterisk display indicating low reliability is given to the display region SC9a in the analysis result of the basic item of the sample measured by the non-dedicated reagent (non-genuine product). In the analysis result screen SC10 shown in FIG. 21, the numerical data on the research items of the display region SC10a of the sample measured by the non-dedicated reagent (non-genuine product) is non-displayed by the hyphen sign. As shown in FIG. 22, in the analysis result screen SC11 in which the research 1 tab SC11a is selected, the red blood cell form information of the display region SC11b are all non-displayed by the hyphen sign. The scattergram of the display region SC11 involved therewith is also non-displayed. Furthermore, as shown in FIG. 23, the urine concentration information and the like of the display region SC12b are all non-displayed in the analysis result screen SC12 in a state the research 2 tab SC12a is selected. Thus, when measurement is conducted with the non-dedicated reagent (non-genuine product), the asterisk display indicating low reliability (see FIGS. 19 and 20) is given to the numerical data of the basic item in the analysis result screen SC8 to SC12 (see FIGS. 19 to 23). The analysis results other than the numerical data of the basic items are all non-displayed. Thus, limitation is made such that the analysis results are not displayed as much as possible when the reliability of the analysis result is low. When doctors diagnose the patient, the analysis result of the sample collected from the patient is referenced, but the doctors may perform a more detailed diagnosis by referencing the distribution diagram of the scattergram, the histogram, and the like, and the numerical data of the research items and not only the numerical data of the basic items. However, the analysis result in which the non-dedicated reagent is used has low reliability, and the diagnosis itself becomes diagnosis of low reliability if the detailed diagnosis is performed using such analysis result. The scattergram and the analysis result of the research items used when performing the detailed diagnosis are not displayed, so that detailed diagnosis is prevented from being made with the analysis result of low reliability.

In the present embodiment, the display 32 for displaying the analysis result, and the CPU 31a which determines whether the reagent is appropriate for the measurement of the urine particles by the measurement section 2 based on the reagent code 100a accepted at the reagent change screen SC4 (FIG. 8), and controls the display by the display 32 based on the result of determination are arranged, as described above. According to such configuration, reagent is determined as not appropriate by the CPU 31a when the non-dedicated reagent (non-genuine product) not appropriate for analysis is used. The display 32 can be controlled such that the asterisk display (*) enabling the user to recognize that the analysis result is of low reliability is displayed. As a result, the user recognizes that the analysis result has low reliability.

In the present embodiment, the CPU 31a controls the display by the display 32 so as to display the warning screen SC6 (FIG. 14) when determined that the reagent is the non-appropriate non-dedicated reagent (non-genuine product). According to such configuration, the user can easily recognize the low reliability of the analysis result.

In the present embodiment, the CPU 31a is configured to determine whether the reagent is the dedicated reagent (genuine product) appropriate for the analysis of the urine particles by the measurement section 2, based on both the reagent code 100a and the reagent remaining quantity information accepted by the reagent change screen SC4. According to such configuration, the CPU 31a may determine at high accuracy whether the reagent is the dedicated reagent (genuine product) since determination can be made based not only on the reagent code 100a, but also on the measurement result of the reagent remaining quantity.

The embodiments disclosed herein are merely illustrative in all aspects and should not be construed as being restrictive. The scope of the invention is defined by the appended claims rather than by the description preceding them, and all changes that fall within meets and bounds of the claims, or equivalence of such meets and bounds are therefore intended to be embraced by the claims.

For instance, an example where the present invention is applied to the urine particle analyzer serving as one example of the sample analyzer has been shown in each embodiment. However, the present invention is not limited thereto. As long as the apparatus is a sample analyzer that analyzes the sample using a dedicated reagent, the present invention may be applied to other types of sample analyzers such as such as multiple blood cell analyzer, blood coagulation measurement apparatus, immune analyzer, and the like.

An example of displaying the warning screen in activation has been shown in each embodiment. However, the present invention is not limited thereto. The warning screen may be displayed every time the analysis result screen is displayed.

Figure 17:
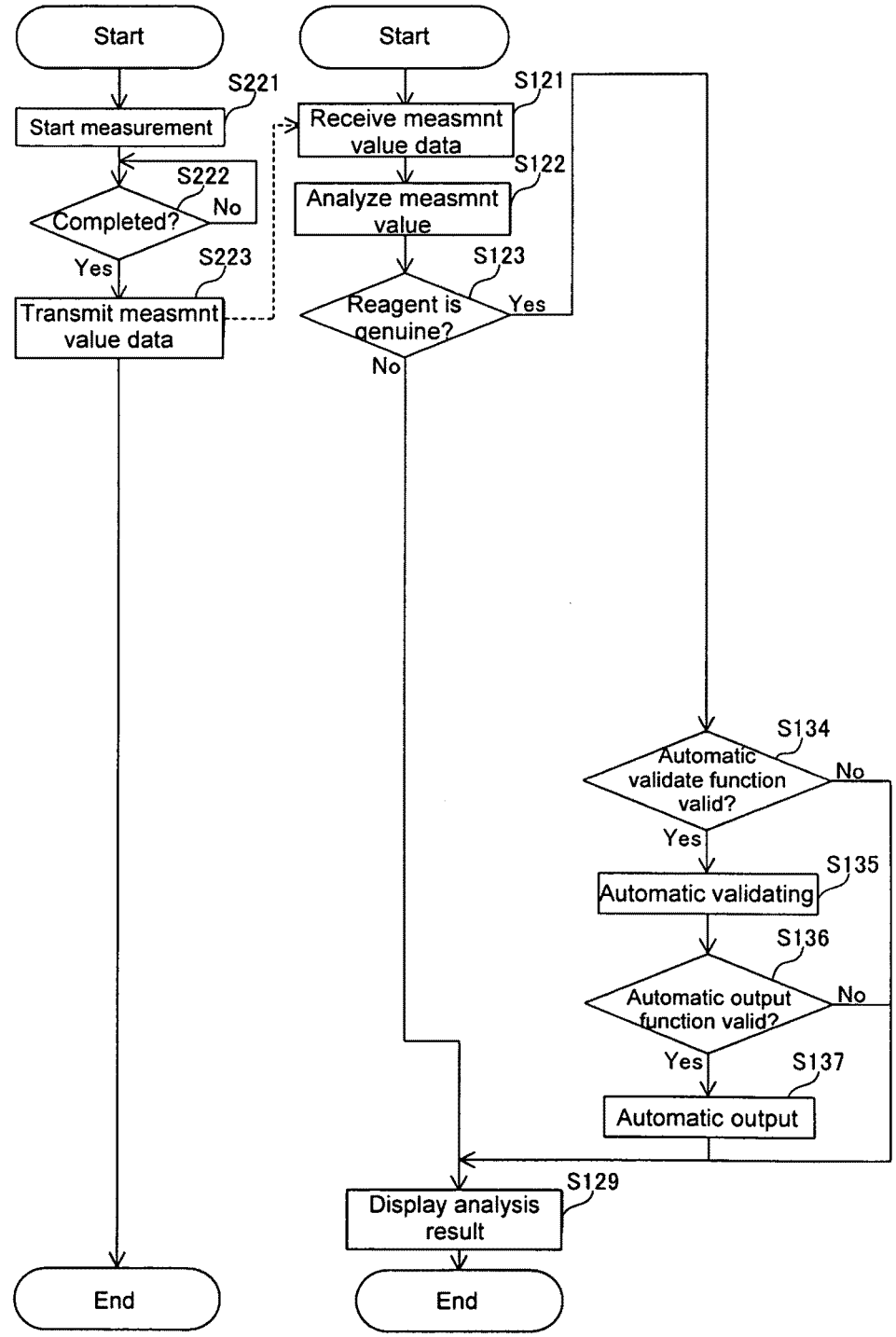
FIG. 17 is a flowchart describing a variant of the measurement and analyzing operation of the urine particle analyzer according to one embodiment of the present invention.

In the first embodiment, an example of performing the updating process of the invalid flag and returning the function of the invalid state to the valid state based on the mode of the invalid flag in the measurement and analyzing operation has been shown. However, the present invention is not limited thereto. As shown in FIG. 17, the operations of steps S124 to S128 and steps S130 to S133 of FIG. 15 may not be performed. Thus, similar to the above embodiment, the automatic validate function and the automatic output function may not be operated when the non-dedicated reagent is used.

In each embodiment, an example of applying the present invention to the sample analyzer for analyzing the sample using one reagent has been shown. However, the present invention is not limited thereto. The present invention may be applied to the sample analyzer for analyzing the sample using a plurality of reagents. In this case, in the first embodiment, for example, the automatic validate function and the automatic output function may be changed to an invalid state when the non-dedicated reagent (non-genuine product) is used for one of the reagents of the plurality of reagents. The automatic validate function and the automatic output function may be changed to the invalid state when the non-dedicated reagent (non-genuine product) is used in a predetermined one reagent or a predetermined plurality of reagents.

In the second embodiment, the display of the analysis result may be limited when the non-dedicated reagent (non-genuine product) is used in the one of the plurality of reagents. The display of the analysis result may be limited when the non-dedicated reagent (non-genuine product) is used in the predetermined one reagent or the predetermined plurality of reagents.

An example where both the automatic validate function and the automatic output function are changed to the invalid state when the non-dedicated reagent is used has been described in the first embodiment, but the present invention is not limited thereto, and the automatic validate function may be changed to the invalid state without changing the automatic output function to the invalid state.

Furthermore, in each embodiment, an example where the analysis result can be output to the host computer, the slip printer, and the graphic printer has been shown. However, the present invention is not limited thereto. For instance, the analysis result may be computerized to a PDF file and the like.

In the second embodiment, the display of the analysis result is limited when determined that the reagent is not appropriate (non-genuine product). However, the present invention is not limited thereto. The analyzing operation may be executed when determined that the reagent is appropriate, and the analyzing operation may be prohibited when determined that the reagent is not appropriate. Thus, the analysis result of low reliability is prevented from being provided to the user.

In each embodiment, the encryption algorithm used in the reagent code is MD5. However, the present invention is not limited thereto. Other encryption algorithm such as SHA and MD4 may be used.

In each embodiment, whether the reagent is the dedicated reagent (genuine product) or the non-dedicated reagent (non-genuine product) is determined. However, the present invention is not limited thereto. In addition to the determination on whether the reagent is a dedicated reagent, the expiration date and the date of measurement of the reagent may be compared, and whether or not the reagent is expired may be determined. In the first embodiment, the automatic validation process and the automatic output process are executed without limitation if the reagent is not expired, and at least either the automatic validation process or the automatic output process is limited if expired.

In the second embodiment, the analyzing operation is executed when the reagent is not expired, and a warning screen notifying that the reagent is expired is displayed and the analyzing operation is prohibited if the reagent is expired.

What is claimed is:

1. A sample analyzer comprising:
an analysis section configured for analyzing a sample containing particles by using a reagent and obtaining numerical data and distribution diagram of the particles contained in the sample;
a display device for displaying an analysis result by the analysis section;
an information receiver for receiving an input of reagent information assigned to the reagent;
a determination section configured for determining whether or not the reagent satisfies a condition to determine that the reagent is a genuine product based on the reagent information received by the information receiver; and
a controller configured for controlling an operation of the sample analyzer based on a result of the determination by the determination section,
wherein the controller controls the display device to display both the numerical data and the distribution diagram as the analysis result if determined that the reagent satisfies the condition by the determination section and to display the numerical data without displaying the distribution diagram as the analysis result if determined that the reagent does not satisfy the condition by the determination section.

2. The sample analyzer according to claim 1, wherein if determined that the reagent does not satisfy the condition by the determination section, the controller controls the display device to display low reliability of the analysis result by the analysis section with the analysis result.

3. The sample analyzer according to claim 1, wherein the controller controls the display device to display a warning that the reliability of the analysis result is low if determined that the reagent does not satisfy the condition by the determination section.

4. The sample analyzer according to claim 3, wherein the controller controls the display device so as to display the warning at least in start up of the sample analyzer.

5. The sample analyzer according to claim 1, wherein the controller prohibits the analyzing operation by the analysis section if determined that the reagent does not satisfy the condition by the determination section.

6. The sample analyzer according to claim 1, wherein the controller automatically validates the analysis result by the analysis section if determined that the reagent satisfies the condition by the determination section, and does not automatically validate the analysis result if determined that the reagent does not satisfy the condition by the determination section.

7. The sample analyzer according to claim 1, wherein the distribution diagram is a scattergram or histogram.

8. The sample analyzer according to claim 1, wherein the analysis section comprises: a light emitter to emit a light; a flow cell in which the sample flows, the flow cell being arranged to be irradiated with the light; and one or more light receivers to detect light emitted from the flow cell.

9. The sample analyzer according to claim 8, wherein the one or more light receivers are arranged to receive forward scattered light emitted from the flow cell and/or lateral scattered light emitted from the flow cell and/or fluorescent light emitted from the flow cell.

10. The sample analyzer according to claim 1, wherein the sample is urine.

11. The sample analyzer according to claim 10, wherein the numerical data includes at least one of: number of red blood cells; number of white blood cells; number of epidermal cells; number of casts; and number of bacteria.

12. The sample analyzer according to claim 10, wherein when the controller controls the display device to display the distribution diagram, the distribution diagram is displayed to show distribution of one of red blood cells; white blood cells; epidermal cells; casts; and bacteria.

13. The sample analyzer according to claim 1, wherein the reagent is contained in a container to which the reagent information is assigned.

14. The sample analyzer according to claim 13, wherein the reagent information is assigned to the reagent container in the form of a bar code.

15. The sample analyzer according to claim 14, further comprising a bar code reader, wherein the information receiver is configured to receive the input of reagent information read by the bar code reader.

16. The sample analyzer according to claim 13, wherein the reagent information is assigned to the reagent container in the form of alpha-numerical characters.

17. The sample analyzer according to claim 16, further comprising an input device through which a user inputs alpha-numerical characters, wherein the information receiver is configured to receive the input of reagent information input by the user through the input device.

* * * * *